(12) United States Patent
Bell et al.

(10) Patent No.: US 11,690,683 B2
(45) Date of Patent: *Jul. 4, 2023

(54) VISION-BASED POSITION AND ORIENTATION DETERMINATION FOR ENDOVASCULAR TOOLS

(71) Applicant: Remedy Robotics, Inc., San Francisco, CA (US)

(72) Inventors: David James Bell, San Francisco, CA (US); Jake Anthony Sganga, San Francisco, CA (US); Gregory Kahn, Berkeley, CA (US)

(73) Assignee: REMEDY ROBOTICS, INC, San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/810,102

(22) Filed: Jun. 30, 2022

(65) Prior Publication Data

US 2023/0000563 A1    Jan. 5, 2023

Related U.S. Application Data

(60) Provisional application No. 63/264,531, filed on Nov. 24, 2021, provisional application No. 63/202,963, filed on Jul. 1, 2021.

(51) Int. Cl.
*A61B 34/20* (2016.01)
*A61B 90/00* (2016.01)
*A61B 34/30* (2016.01)

(52) U.S. Cl.
CPC .............. *A61B 34/20* (2016.02); *A61B 90/36* (2016.02); *A61B 90/39* (2016.02);
(Continued)

(58) Field of Classification Search
CPC . A61B 34/20; A61B 90/39; A61B 2034/2065; A61B 2034/301;
(Continued)

(56) References Cited

U.S. PATENT DOCUMENTS

| 819,885 A | 5/1906 | Holmen |
| 5,456,574 A | 10/1995 | Bos et al. |

(Continued)

FOREIGN PATENT DOCUMENTS

| CN | 105125241 | 12/2015 |
| DE | 20 2012 006 263 | 9/2013 |

(Continued)

OTHER PUBLICATIONS

Adeoye O, Albright K, Carr B, et al., "Geographic access to acute stroke care in the United States." Stroke. 2014. 45:3019-3024.

(Continued)

*Primary Examiner* — Amelie R Davis
(74) *Attorney, Agent, or Firm* — Knobbe Martens Olson & Bear LLP

(57) ABSTRACT

Systems and methods for vision-based position and orientation determination for endovascular tools are disclosed. In one example, a method includes receiving a two-dimensional medical image including a view of at least a distal portion of a medical instrument, the distal portion of the medical instrument including one or more fiducials positioned thereon, the one or more fiducials being radio-opaque and visible in the medical image. The method also includes detecting, within the medical image, a two-dimensional appearance of the one or more fiducials, and based on the two-dimensional appearance of the one or more fiducials, determining at least one of a roll angle of the distal portion of the medical instrument, and an incline of the distal portion of the medical instrument.

20 Claims, 26 Drawing Sheets

(52) U.S. Cl.
CPC . *A61B 2034/2065* (2016.02); *A61B 2034/301* (2016.02); *A61B 2090/363* (2016.02); *A61B 2090/376* (2016.02); *A61B 2090/3966* (2016.02)

(58) Field of Classification Search
CPC ........ A61B 2090/363; A61B 2090/376; A61B 2090/3966; A61B 34/30–70
See application file for complete search history.

(56) References Cited

U.S. PATENT DOCUMENTS

| | | | |
|---|---|---|---|
| 5,607,393 | A | 3/1997 | Ensminger et al. |
| 5,792,123 | A | 8/1998 | Ensminger |
| 6,132,368 | A | 10/2000 | Cooper |
| 6,171,329 | B1 | 1/2001 | Shaw et al. |
| 6,203,568 | B1 | 3/2001 | Lombardi et al. |
| 6,361,557 | B1 | 3/2002 | Gittings et al. |
| 6,522,933 | B2 | 2/2003 | Nguyen |
| 6,572,610 | B2 | 6/2003 | Kovalcheck et al. |
| 6,592,581 | B2 | 7/2003 | Bowe |
| 6,602,267 | B2 | 8/2003 | Castaneda |
| 6,623,508 | B2 | 9/2003 | Shaw et al. |
| 6,645,218 | B1 | 11/2003 | Cassidy et al. |
| 6,648,875 | B2 | 11/2003 | Simpson et al. |
| 6,652,506 | B2 | 11/2003 | Bowe et al. |
| 6,669,692 | B1 | 12/2003 | Nelson |
| 6,743,239 | B1 | 6/2004 | Kuehn et al. |
| 6,858,005 | B2 | 2/2005 | Ohline et al. |
| 6,860,878 | B2 | 3/2005 | Brock |
| 6,869,414 | B2 | 3/2005 | Simpson et al. |
| 6,872,433 | B2 | 3/2005 | Seward et al. |
| 6,926,711 | B2 | 8/2005 | Lentz et al. |
| 6,979,312 | B2 | 12/2005 | Shimada |
| 6,986,769 | B2 | 1/2006 | Nelson et al. |
| 7,011,655 | B2 | 3/2006 | Thompson et al. |
| 7,052,489 | B2 | 5/2006 | Griego et al. |
| 7,122,020 | B2 | 10/2006 | Mogul |
| 7,285,108 | B2 | 10/2007 | Koerner et al. |
| 7,331,967 | B2 | 2/2008 | Lee et al. |
| 7,357,774 | B2 | 4/2008 | Cooper |
| 7,379,790 | B2 | 5/2008 | Toth |
| 7,419,477 | B2 | 9/2008 | Simpson et al. |
| 7,503,914 | B2 | 3/2009 | Coleman et al. |
| 7,608,056 | B2 | 10/2009 | Kennedy, II |
| 7,615,044 | B2 | 11/2009 | Scheibe et al. |
| 7,717,875 | B2 | 5/2010 | Knudson et al. |
| 7,731,706 | B2 | 6/2010 | Potter |
| 7,758,569 | B2 | 7/2010 | Brock |
| 7,789,875 | B2 | 9/2010 | Brock et al. |
| 7,803,130 | B2 | 9/2010 | Ryan et al. |
| 7,819,884 | B2 | 10/2010 | Lee et al. |
| 7,840,261 | B2 | 11/2010 | Rosenman et al. |
| 7,942,854 | B1 | 5/2011 | Von Oepen et al. |
| 7,947,050 | B2 | 5/2011 | Lee et al. |
| 7,947,051 | B2 | 5/2011 | Lee et al. |
| 7,963,913 | B2 | 6/2011 | Devengenzo et al. |
| 7,972,323 | B1 | 7/2011 | Bencini et al. |
| 8,000,764 | B2 | 8/2011 | Rashidi |
| 8,002,739 | B2 | 8/2011 | Lee et al. |
| 8,016,784 | B1 | 9/2011 | Hayzelden et al. |
| 8,052,607 | B2 | 11/2011 | Byrd |
| 8,062,212 | B2 | 11/2011 | Belson |
| 8,066,664 | B2 | 11/2011 | LaDuca et al. |
| 8,118,803 | B1 | 2/2012 | Chow |
| 8,137,263 | B2 | 3/2012 | Marescaux et al. |
| 8,142,367 | B2 | 3/2012 | Gardeski et al. |
| 8,162,934 | B2 | 4/2012 | Potter |
| 8,170,657 | B1 | 5/2012 | Ehrenreich |
| 8,182,470 | B2 | 5/2012 | Devengenzo et al. |
| 8,192,399 | B2 | 6/2012 | Birchard |
| 8,214,019 | B2 | 7/2012 | Govari et al. |
| 8,218,846 | B2 | 7/2012 | Trumer et al. |
| 8,231,610 | B2 | 7/2012 | Jo et al. |
| 8,251,977 | B2 | 8/2012 | Partlett |
| 8,256,428 | B2 | 9/2012 | Hindricks et al. |
| 8,273,016 | B2 | 9/2012 | O'Sullivan |
| 8,273,054 | B2 | 9/2012 | St. Germain et al. |
| 8,295,943 | B2 | 10/2012 | Eggen et al. |
| 8,298,177 | B2 | 10/2012 | Selkee |
| 8,303,576 | B2 | 11/2012 | Brock |
| 8,348,931 | B2 | 1/2013 | Cooper et al. |
| 8,372,033 | B2 | 2/2013 | Kronstedt et al. |
| 8,388,572 | B2 | 3/2013 | Olsen et al. |
| 8,409,245 | B2 | 4/2013 | Lee |
| 8,409,273 | B2 | 4/2013 | Thornton et al. |
| 8,414,598 | B2 | 4/2013 | Brock et al. |
| 8,460,236 | B2 | 6/2013 | Roelle et al. |
| 8,486,022 | B2 | 7/2013 | Ludwig et al. |
| 8,506,555 | B2 | 8/2013 | Morales |
| 8,506,562 | B2 | 8/2013 | Anderson et al. |
| 8,517,923 | B2 | 8/2013 | Belson et al. |
| 8,529,582 | B2 | 9/2013 | Devengenzo et al. |
| 8,568,435 | B2 | 10/2013 | Pillai et al. |
| 8,603,135 | B2 | 12/2013 | Mueller |
| 8,607,935 | B2 | 12/2013 | Goldberg et al. |
| 8,608,773 | B2 | 12/2013 | Tierney et al. |
| 8,620,400 | B2 | 12/2013 | de la Rama et al. |
| 8,632,468 | B2 | 1/2014 | Glossop et al. |
| 8,636,764 | B2 | 1/2014 | Miles et al. |
| 8,641,602 | B2 | 2/2014 | Belson |
| 8,641,700 | B2 | 2/2014 | Devengenzo et al. |
| 8,647,362 | B2 | 2/2014 | Griego |
| 8,671,817 | B1 | 3/2014 | Bogusky |
| 8,672,837 | B2 | 3/2014 | Roelle et al. |
| 8,672,922 | B2 | 3/2014 | Loh et al. |
| 8,690,871 | B2 | 4/2014 | Partlett et al. |
| 8,706,260 | B2 | 4/2014 | Stewart et al. |
| 8,709,037 | B2 | 4/2014 | Lee et al. |
| 8,715,318 | B2 | 5/2014 | Miles et al. |
| 8,721,530 | B2 | 5/2014 | Ohline et al. |
| D708,740 | S | 7/2014 | Osypka et al. |
| 8,808,169 | B2 | 8/2014 | Macnamara et al. |
| 8,808,278 | B2 | 8/2014 | Goldberg et al. |
| 8,827,948 | B2 | 9/2014 | Romo et al. |
| 8,834,489 | B2 | 9/2014 | Cooper et al. |
| 8,840,560 | B2 | 9/2014 | Hossack et al. |
| 8,864,656 | B2 | 10/2014 | Konstorum |
| D718,437 | S | 11/2014 | Osypka |
| 8,894,610 | B2 | 11/2014 | Macnamara et al. |
| 8,920,429 | B2 | 12/2014 | Hinman et al. |
| 8,939,960 | B2 | 1/2015 | Rosenman et al. |
| 8,961,533 | B2 | 2/2015 | Stahler et al. |
| 8,979,740 | B2 | 3/2015 | Butler |
| 9,005,217 | B2 | 4/2015 | Govari et al. |
| 9,023,060 | B2 | 5/2015 | Cooper et al. |
| 9,061,120 | B2 | 6/2015 | Osypka et al. |
| 9,084,621 | B2 | 7/2015 | Weitzner et al. |
| 9,085,085 | B2 | 7/2015 | Danitz et al. |
| 9,089,356 | B2 | 7/2015 | Chen et al. |
| 9,095,253 | B2 | 8/2015 | Hinman et al. |
| 9,101,379 | B2 | 8/2015 | Au et al. |
| 9,101,735 | B2 | 8/2015 | Rothe et al. |
| 9,107,673 | B2 | 8/2015 | Chong et al. |
| 9,114,232 | B2 | 8/2015 | Olson et al. |
| 9,138,166 | B2 | 9/2015 | Wong et al. |
| 9,149,937 | B2 | 10/2015 | Goldberg et al. |
| 9,155,449 | B2 | 10/2015 | Danitz et al. |
| 9,173,551 | B2 | 11/2015 | Peters et al. |
| 9,173,713 | B2 | 11/2015 | Hart et al. |
| 9,186,046 | B2 | 11/2015 | Ramamurthy et al. |
| 9,199,061 | B2 | 12/2015 | Selkee |
| 9,204,933 | B2 | 12/2015 | Reis et al. |
| 9,241,770 | B2 | 1/2016 | Stokes et al. |
| 9,254,372 | B2 | 2/2016 | Ryan |
| 9,259,271 | B2 | 2/2016 | Anvari et al. |
| 9,308,349 | B2 | 4/2016 | Rezac et al. |
| 9,314,587 | B2 | 4/2016 | Arnim et al. |
| 9,314,591 | B2 | 4/2016 | Ogle |
| 9,326,822 | B2 | 5/2016 | Lewis et al. |
| 9,333,324 | B2 | 5/2016 | Cohen et al. |
| 9,351,716 | B2 | 5/2016 | Miles et al. |
| 9,364,636 | B2 | 6/2016 | Grewe et al. |
| 9,370,868 | B2 | 6/2016 | Danitz et al. |

(56) References Cited

U.S. PATENT DOCUMENTS

| | | |
|---|---|---|
| 9,399,300 B2 | 7/2016 | Goldberg et al. |
| 9,427,282 B2 | 8/2016 | Belson et al. |
| 9,434,077 B2 | 9/2016 | Danitz et al. |
| 9,439,732 B2 | 9/2016 | Devengenzo et al. |
| 9,474,527 B1 | 10/2016 | Knodel et al. |
| 9,477,301 B2 | 10/2016 | Kishi |
| 9,480,533 B2 | 11/2016 | Devengenzo et al. |
| 9,492,192 B2 | 11/2016 | To et al. |
| 9,498,602 B2 | 11/2016 | Osypka et al. |
| 9,504,371 B2 | 11/2016 | Mitchell et al. |
| 9,504,372 B2 | 11/2016 | Kim |
| 9,510,885 B2 | 12/2016 | Burger et al. |
| 9,517,326 B2 | 12/2016 | Hinman et al. |
| 9,533,122 B2 | 1/2017 | Weitzner et al. |
| 9,572,957 B2 | 2/2017 | Osypka et al. |
| D782,037 S | 3/2017 | Osypka et al. |
| 9,585,647 B2 | 3/2017 | Clark |
| 9,597,514 B2 | 3/2017 | Khairkhahan et al. |
| 9,622,729 B2 | 4/2017 | Dewaele et al. |
| 9,636,483 B2 | 5/2017 | Hart et al. |
| 9,642,514 B2 | 5/2017 | Gilboa |
| 9,662,473 B2 | 5/2017 | McDaniel et al. |
| 9,675,422 B2 | 6/2017 | Hourtash et al. |
| 9,693,759 B2 | 7/2017 | Seguy |
| 9,693,780 B2 | 7/2017 | Miles et al. |
| 9,713,509 B2 | 7/2017 | Schuh et al. |
| 9,724,163 B2 | 8/2017 | Orban |
| 9,737,365 B2 | 8/2017 | Hegeman et al. |
| 9,737,371 B2 | 8/2017 | Romo et al. |
| 9,743,990 B2 | 8/2017 | Au et al. |
| 9,744,335 B2 | 8/2017 | Jiang |
| 9,750,577 B2 | 9/2017 | Pacheco et al. |
| 9,757,149 B2 | 9/2017 | Cooper et al. |
| 9,757,538 B2 | 9/2017 | Kimmel et al. |
| 9,763,741 B2 | 9/2017 | Alvarez et al. |
| 9,775,963 B2 | 10/2017 | Miller |
| 9,782,130 B2 | 10/2017 | Hauck et al. |
| 9,814,490 B2 | 11/2017 | Neoh et al. |
| 9,844,412 B2 | 12/2017 | Bogusky et al. |
| 9,848,949 B2 | 12/2017 | Osypka |
| 9,861,790 B2 | 1/2018 | Selkee |
| 9,867,982 B2 | 1/2018 | Berthiaume et al. |
| 9,877,781 B2 | 1/2018 | Grasse et al. |
| 9,883,864 B2 | 2/2018 | Miles et al. |
| 9,889,273 B2 | 2/2018 | Cully et al. |
| 9,895,813 B2 | 2/2018 | Blumenkranz et al. |
| 9,901,408 B2 | 2/2018 | Larkin |
| 9,907,570 B2 | 3/2018 | Osypka et al. |
| 9,913,684 B2 | 3/2018 | Osypka |
| 9,937,322 B2 | 4/2018 | Drake et al. |
| 9,949,749 B2 | 4/2018 | Noonan et al. |
| 9,955,986 B2 | 5/2018 | Shah |
| 9,956,051 B2 | 5/2018 | Stokes et al. |
| 9,962,066 B2 | 5/2018 | Rogers et al. |
| 9,968,241 B2 | 5/2018 | Iuel |
| 9,974,619 B2 | 5/2018 | Goldenberg et al. |
| 9,993,211 B2 | 6/2018 | Tokuda et al. |
| 9,993,313 B2 | 6/2018 | Schuh et al. |
| 10,010,367 B2 | 7/2018 | Chien et al. |
| 10,010,699 B2 | 7/2018 | Cohen et al. |
| 10,010,700 B2 | 7/2018 | Romoscanu |
| 10,016,187 B2 | 7/2018 | Castro |
| 10,016,191 B2 | 7/2018 | Kaiser et al. |
| 10,029,073 B2 | 7/2018 | Kabe et al. |
| 10,029,074 B2 | 7/2018 | Mogul |
| 10,035,002 B2 | 7/2018 | Weiss |
| 10,039,436 B2 | 8/2018 | Tah et al. |
| 10,076,337 B2 | 9/2018 | Miles et al. |
| 10,080,608 B2 | 9/2018 | Datta et al. |
| 10,099,036 B2 | 10/2018 | Heideman et al. |
| 10,130,427 B2 | 11/2018 | Tanner et al. |
| 10,143,360 B2 | 12/2018 | Roelle et al. |
| 10,159,533 B2 | 12/2018 | Moll et al. |
| 10,173,073 B2 | 1/2019 | Webler, Jr. et al. |
| 10,188,273 B2 | 1/2019 | Tilson et al. |
| 10,188,832 B2 | 1/2019 | Salahieh et al. |
| 10,201,394 B2 | 2/2019 | Yanagihara et al. |
| 10,219,874 B2 | 3/2019 | Yu et al. |
| 10,238,837 B2 | 3/2019 | Duindam et al. |
| 10,265,502 B2 | 4/2019 | Tsai et al. |
| 10,286,183 B2 | 5/2019 | Flygare et al. |
| 10,292,719 B2 | 5/2019 | Burger et al. |
| 10,300,286 B2 | 5/2019 | Ward et al. |
| 10,307,214 B2 | 6/2019 | Lathrop et al. |
| 10,321,923 B2 | 6/2019 | DeGraaf et al. |
| 10,321,964 B2 | 6/2019 | Grover et al. |
| 10,327,625 B2 | 6/2019 | Belson et al. |
| 10,335,243 B2 | 7/2019 | Yanagihara et al. |
| 10,342,411 B2 | 7/2019 | Japerson et al. |
| 10,342,625 B2 | 7/2019 | Loh et al. |
| 10,349,943 B2 | 7/2019 | Noonan et al. |
| 10,363,109 B2 | 7/2019 | Dachs et al. |
| 10,376,170 B2 | 8/2019 | Quinn et al. |
| 10,398,499 B2 | 9/2019 | Clark et al. |
| 10,405,939 B2 | 9/2019 | Romo |
| 10,405,940 B2 | 9/2019 | Romo |
| 10,413,708 B2 | 9/2019 | Loh |
| 10,426,557 B2 | 10/2019 | Amiri et al. |
| 10,426,560 B2 | 10/2019 | Bowling et al. |
| 10,454,347 B2 | 10/2019 | Covington et al. |
| 10,456,166 B2 | 10/2019 | Cooper et al. |
| 10,463,439 B2 | 11/2019 | Joseph et al. |
| 10,463,440 B2 | 11/2019 | Bowling et al. |
| 10,470,830 B2 | 11/2019 | Hill et al. |
| 10,478,296 B2 | 11/2019 | Le et al. |
| 10,482,599 B2 | 11/2019 | Mintz et al. |
| 10,485,621 B2 | 11/2019 | Morrissette et al. |
| 10,493,239 B2 | 12/2019 | Hart et al. |
| 10,493,241 B2 | 12/2019 | Jiang |
| 10,500,373 B2 | 12/2019 | Barrish et al. |
| 10,507,063 B2 | 12/2019 | Zuhars |
| 10,512,757 B2 | 12/2019 | Laby et al. |
| 10,525,233 B2 | 1/2020 | Barrish et al. |
| 10,525,257 B2 | 1/2020 | Govea et al. |
| 10,537,385 B2 | 1/2020 | Wu et al. |
| 10,537,713 B2 | 1/2020 | Kidd et al. |
| 10,543,047 B2 | 1/2020 | Yu |
| 10,555,780 B2 | 2/2020 | Tanner et al. |
| 10,556,092 B2 | 2/2020 | Yu et al. |
| 10,568,708 B2 | 2/2020 | Au et al. |
| 10,575,745 B2 | 3/2020 | Solis |
| 10,576,243 B2 | 3/2020 | Suon et al. |
| 10,582,929 B2 | 3/2020 | Miles et al. |
| 10,583,271 B2 | 3/2020 | Bogusky |
| 10,588,495 B2 | 3/2020 | Simmons et al. |
| 10,588,620 B2 | 3/2020 | Caffes et al. |
| 10,603,124 B2 | 3/2020 | Camarillo et al. |
| 10,610,312 B2 | 4/2020 | Srivastava et al. |
| 10,610,320 B2 | 4/2020 | Dachs et al. |
| 10,617,402 B2 | 4/2020 | Reddy et al. |
| 10,617,848 B2 | 4/2020 | Weitzner et al. |
| 10,631,937 B2 | 4/2020 | Tyulmankov et al. |
| 10,631,949 B2 | 4/2020 | Schuh et al. |
| 10,632,281 B2 | 4/2020 | Rosenman et al. |
| 10,646,696 B2 | 5/2020 | Barrish et al. |
| 10,667,871 B2 | 6/2020 | Romo et al. |
| 10,682,503 B2 | 6/2020 | Gerrans et al. |
| 10,687,691 B2 | 6/2020 | Smith et al. |
| 10,695,536 B2 | 6/2020 | Weitzner et al. |
| 10,709,512 B2 | 7/2020 | Bajo et al. |
| 10,737,064 B1 | 8/2020 | Ju |
| 10,737,073 B2 | 8/2020 | Barrish et al. |
| 10,744,303 B2 | 8/2020 | Duindam et al. |
| 10,758,310 B2 | 9/2020 | Shelton, IV |
| 10,758,714 B2 | 9/2020 | Laby et al. |
| 10,765,486 B2 | 9/2020 | Bajo et al. |
| 10,772,637 B2 | 9/2020 | Miles et al. |
| 10,779,710 B2 | 9/2020 | Matthison-Hansen |
| 10,779,803 B2 | 9/2020 | Prisco et al. |
| 10,779,898 B2 | 9/2020 | Hill et al. |
| 10,786,329 B2 | 9/2020 | Schuh et al. |
| 10,792,061 B2 | 10/2020 | Dewaele et al. |
| 10,792,464 B2 | 10/2020 | Romo et al. |
| 10,792,468 B2 | 10/2020 | Bolduc et al. |

(56) References Cited

U.S. PATENT DOCUMENTS

| | | |
|---|---|---|
| 10,799,096 B2 | 10/2020 | Golden et al. |
| 10,799,224 B2 | 10/2020 | Tasci |
| 10,806,897 B2 | 10/2020 | Furnish |
| 10,806,899 B2 | 10/2020 | Laby et al. |
| 10,813,708 B2 | 10/2020 | Reinstein et al. |
| 10,814,101 B2 | 10/2020 | Jiang |
| 10,814,102 B2 | 10/2020 | Laby et al. |
| 10,881,832 B2 | 1/2021 | Chu |
| 10,932,877 B2 | 3/2021 | Devengenzo et al. |
| 10,939,972 B2 | 3/2021 | Au |
| 10,939,973 B2 | 3/2021 | DiMaio et al. |
| 10,944,728 B2 | 3/2021 | Wiener |
| 11,058,508 B2 | 7/2021 | Scheib et al. |
| 11,129,685 B2 | 9/2021 | Zemlok et al. |
| 11,160,621 B2 | 11/2021 | Steger |
| 11,213,362 B2 | 1/2022 | Sharon et al. |
| 11,241,291 B2 | 2/2022 | Sharon et al. |
| 11,259,881 B2 | 3/2022 | Kilroy et al. |
| 11,284,956 B2 | 3/2022 | Zemlok et al. |
| 11,318,297 B2 | 5/2022 | Li et al. |
| 11,369,450 B2 | 6/2022 | Bernstein |
| 11,406,465 B2 | 8/2022 | Zemlok et al. |
| 11,419,691 B2 | 8/2022 | Kim et al. |
| 11,446,105 B2 | 9/2022 | Dachs et al. |
| 2007/0078334 A1 | 4/2007 | Scully |
| 2008/0119872 A1 | 5/2008 | Brock et al. |
| 2008/0125793 A1 | 5/2008 | Brock et al. |
| 2008/0125794 A1 | 5/2008 | Brock et al. |
| 2008/0177285 A1 | 7/2008 | Brock et al. |
| 2008/0228065 A1 | 9/2008 | Viswanathan et al. |
| 2008/0262301 A1 | 10/2008 | Gibbons et al. |
| 2008/0319314 A1 | 12/2008 | Hill et al. |
| 2009/0105700 A1 | 4/2009 | Anderson |
| 2009/0171147 A1 | 7/2009 | Lee et al. |
| 2009/0324161 A1 | 12/2009 | Prisco |
| 2010/0204646 A1 | 8/2010 | Plicchi et al. |
| 2010/0234938 A1 | 9/2010 | Taheri et al. |
| 2010/0249497 A1 | 9/2010 | Peine et al. |
| 2011/0046441 A1 | 2/2011 | Wiltshire et al. |
| 2011/0066161 A1 | 3/2011 | Cooper |
| 2011/0154473 A1 | 6/2011 | Anderson et al. |
| 2011/0213383 A1 | 9/2011 | Lee et al. |
| 2011/0276034 A1 | 11/2011 | Tomarelli et al. |
| 2011/0319714 A1 | 12/2011 | Roelle et al. |
| 2012/0016311 A1 | 1/2012 | Altman et al. |
| 2012/0253324 A1 | 10/2012 | Lee et al. |
| 2012/0287238 A1* | 11/2012 | Onishi .............. A61B 1/0005 348/45 |
| 2013/0041314 A1 | 2/2013 | Dillon |
| 2013/0158509 A1 | 6/2013 | Consigny et al. |
| 2013/0253469 A1 | 9/2013 | Freed |
| 2015/0045696 A1 | 2/2015 | Osypka |
| 2015/0057610 A1 | 2/2015 | Osypka et al. |
| 2015/0105721 A1 | 4/2015 | Osypka et al. |
| 2015/0164594 A1 | 6/2015 | Romo et al. |
| 2015/0202020 A1 | 7/2015 | Fisher |
| 2015/0335383 A9 | 11/2015 | Cohen |
| 2016/0067457 A1 | 3/2016 | Selkee |
| 2016/0113711 A1 | 4/2016 | Osypka et al. |
| 2016/0213423 A1 | 7/2016 | Kauphusman et al. |
| 2016/0213884 A1 | 7/2016 | Park |
| 2016/0228032 A1 | 8/2016 | Walker et al. |
| 2016/0287226 A1 | 10/2016 | Al-Obani et al. |
| 2017/0106170 A1 | 4/2017 | Hsueh et al. |
| 2017/0224199 A1 | 8/2017 | Demers et al. |
| 2017/0273665 A1 | 9/2017 | Kapoor et al. |
| 2017/0312002 A1 | 11/2017 | Sliwa et al. |
| 2018/0085552 A1 | 3/2018 | Miller |
| 2018/0104007 A1 | 4/2018 | Scheller et al. |
| 2018/0117280 A1 | 5/2018 | Chu |
| 2018/0140177 A1 | 5/2018 | Liu et al. |
| 2018/0207402 A1 | 7/2018 | Tegg |
| 2018/0228557 A1 | 8/2018 | Darisse et al. |
| 2018/0333212 A1 | 11/2018 | Goldenberg et al. |
| 2018/0344979 A1 | 12/2018 | Schultz |
| 2019/0000546 A1 | 1/2019 | Romoscanu |
| 2019/0008601 A1 | 1/2019 | Pereira et al. |
| 2019/0015633 A1 | 1/2019 | Bednarek et al. |
| 2019/0022356 A1 | 1/2019 | Bansal et al. |
| 2019/0076093 A1 | 3/2019 | Saroha et al. |
| 2019/0076160 A1 | 3/2019 | Lin et al. |
| 2019/0105481 A1 | 4/2019 | Lin et al. |
| 2019/0111239 A1 | 4/2019 | Bolduc et al. |
| 2019/0142413 A1 | 5/2019 | Fairneny |
| 2019/0142591 A1 | 5/2019 | Rohl et al. |
| 2019/0151614 A1 | 5/2019 | Hsueh et al. |
| 2019/0209810 A1 | 7/2019 | Reid et al. |
| 2019/0216486 A1 | 7/2019 | Weitzman |
| 2019/0223734 A1 | 7/2019 | Lakkireddy et al. |
| 2019/0224466 A1 | 7/2019 | Oliverius et al. |
| 2019/0254690 A1 | 8/2019 | Cabiri et al. |
| 2019/0255292 A1 | 8/2019 | Osypka et al. |
| 2019/0269368 A1 | 9/2019 | Hauck et al. |
| 2019/0274757 A1 | 9/2019 | Mahapatra et al. |
| 2019/0290886 A1 | 9/2019 | Campbell et al. |
| 2019/0298969 A1 | 10/2019 | Dale et al. |
| 2019/0307517 A1 | 10/2019 | Arai |
| 2019/0314052 A1 | 10/2019 | Thapliyal et al. |
| 2019/0314608 A1 | 10/2019 | Della Vecchia |
| 2019/0321597 A1 | 10/2019 | Van Hoven et al. |
| 2019/0365204 A1 | 12/2019 | Lang et al. |
| 2019/0365536 A1 | 12/2019 | Prabhu |
| 2019/0366040 A1 | 12/2019 | Golden et al. |
| 2019/0388099 A1 | 12/2019 | Zuhars et al. |
| 2020/0015911 A1 | 1/2020 | Yi |
| 2020/0023151 A1 | 1/2020 | Karlsson et al. |
| 2020/0060683 A1 | 2/2020 | Friedman et al. |
| 2020/0060820 A1 | 2/2020 | Ben-Zvi et al. |
| 2020/0069389 A1 | 3/2020 | Morrissette et al. |
| 2020/0078019 A1 | 3/2020 | Dell et al. |
| 2020/0085483 A1 | 3/2020 | Tegg et al. |
| 2020/0100896 A1 | 4/2020 | Jimenez et al. |
| 2020/0138454 A1 | 5/2020 | Patel et al. |
| 2020/0179650 A1 | 6/2020 | Beeckler et al. |
| 2020/0179651 A1 | 6/2020 | Scheltes et al. |
| 2020/0196896 A1 | 6/2020 | Solis |
| 2020/0197111 A1 | 6/2020 | Kim et al. |
| 2020/0222139 A1 | 7/2020 | Dachs et al. |
| 2020/0222667 A1 | 7/2020 | Tang et al. |
| 2020/0230354 A1 | 7/2020 | von Oepen et al. |
| 2020/0230360 A1 | 7/2020 | Yu et al. |
| 2020/0269017 A1 | 8/2020 | Winston et al. |
| 2020/0276415 A1 | 9/2020 | Tang et al. |
| 2020/0289224 A1 | 9/2020 | Johnson et al. |
| 2020/0289789 A1 | 9/2020 | Scheibe et al. |
| 2020/0297444 A1* | 9/2020 | Camarillo .............. G16H 30/40 |
| 2020/0297971 A1 | 9/2020 | Beeckler et al. |
| 2020/0330729 A1 | 10/2020 | Petitpierre et al. |
| 2020/0337766 A1 | 10/2020 | Dando et al. |
| 2020/0337792 A1 | 10/2020 | Zemlok et al. |
| 2020/0383734 A1 | 12/2020 | Dahdouh |
| 2020/0405397 A1* | 12/2020 | Liu .......................... A61B 34/10 |
| 2021/0015573 A1 | 1/2021 | Tsao et al. |
| 2021/0030496 A1 | 2/2021 | Devengenzo et al. |
| 2021/0045626 A1 | 2/2021 | Hsu |
| 2021/0153961 A1 | 5/2021 | DiMaio et al. |
| 2021/0154473 A1 | 5/2021 | Pobiel |
| 2021/0220060 A1 | 7/2021 | Kapadia et al. |
| 2021/0236773 A1 | 8/2021 | Dupont |
| 2021/0267702 A1 | 9/2021 | Kim et al. |
| 2021/0267703 A1 | 9/2021 | Devengenzo et al. |
| 2022/0000570 A1 | 1/2022 | Steger |
| 2022/0008152 A1 | 1/2022 | Daniel |
| 2022/0044057 A1 | 2/2022 | Ganesan et al. |
| 2022/0071723 A1 | 3/2022 | Sharon et al. |
| 2022/0230348 A1 | 7/2022 | Huber et al. |
| 2022/0273388 A1 | 9/2022 | Bernstein |
| 2022/0296321 A1 | 9/2022 | Sharon et al. |
| 2022/0296322 A1 | 9/2022 | Gomez et al. |

(56) References Cited

U.S. PATENT DOCUMENTS

| | | |
|---|---|---|
| 2022/0304758 A1 | 9/2022 | Scheib et al. |
| 2022/0361959 A1 | 11/2022 | Weber et al. |

FOREIGN PATENT DOCUMENTS

| | | |
|---|---|---|
| WO | WO 2013/141011 | 9/2013 |
| WO | WO 2017003453 A1 | 1/2017 |
| WO | WO 2017/070193 | 4/2017 |
| WO | WO 2017115352 A1 | 7/2017 |
| WO | WO 2017/155867 | 9/2017 |
| WO | WO 2018/080470 | 5/2018 |
| WO | WO 2018/204202 | 7/2018 |
| WO | WO 2019/089053 | 5/2019 |
| WO | WO 2019/136357 | 7/2019 |
| WO | WO 2019/156559 | 8/2019 |
| WO | WO 2019/240655 | 12/2019 |
| WO | WO 2020/150709 | 7/2020 |
| WO | WO 2020/187663 | 9/2020 |
| WO | WO 2021/138096 | 7/2021 |
| WO | WO 2022066730 A1 | 3/2022 |

OTHER PUBLICATIONS

Bajo et al.. "Finding Lost Wrenches: Using Continuum Robots for Contact Detection and Estimation of Contact Location." 2010 IEEE International Conference on Robotics and Automation. Anchorage Convention District. May 3-8, 2010, Anchorage, Alaska, USA, pp. 3666-3673.

A. Bajo and N. Simaan, "Kinematics-Based Detection and Localization of Contacts Along Multisegment Continuum Robots," IEEE Transactions on Robotics, vol. 28, No. 2, pp. 291-302, Apr. 2012.

A. Bajo and N. Simaan, "Hybrid motion/force control of multibackbone continuum robots," The International Journal of Robotics Research. 35(4): 422-434. 2016.

J. Burgner-Kahrs, D. C. Rucker, and H. Choset, "Continuum Robots for Medical Applications—A Survey," IEEE Transactions on Robotics, 31(6): 1261-1280, Dec. 2015.

Campbell BCV, De Silva DA, Macleod MR, Coutts SB, Schwamm LH, Davis SM, and Donnan GA, "Ischaemic stroke" (2019) 5(70) Nature Reviews Disease Primers; pp. 1-6.

Comprehensive Stroke Center, The Joint Commission (Web Page) (2021); pp. 1-5.

J. J. Craig, Introduction to Robotics: Mechanics and Control. Pearson Prentice Hall Upper Saddle River, 2005, vol. 3. TOC.

Dasgupta et al., A Fully Convolutional Neural Network Based Structure Prediction Approach towards the Retival Vessel Segmentation, Nov. 16, 2016; pp. 1-4.

A. Degirmenci, P. M. Loschak, C. M. Tschabrunn, E. Anter, and R. D. Howe, "Compensation for Unconstrained Catheter Shaft Motion in Cardiac Catheters," in 2016 IEEE International Conference on Robotics and Automation (ICRA). May 2016, pp. 4436-4442.

C. S. Dela Cruz et al. "Lung Cancer: Epidemiology, Etiology, and Prevention," Clinics in Chest Medicine, vol. 32, No. 4, pp. 605-644, 2011.

International Search Report and Written Opinion for International Application No. PCT/US2021/070726 dated Sep. 17, 2021.

B. Jones and I. Walker, "Kinematics for multisection continuum robots," IEEE Transactions on Robotics, vol. 22, No. 1, pp. 43-55, Feb. 2006.

B. Kim, J. Ha, F. C. Park, and P. E. Dupont, "Optimizing curvature sensor placement for fast, accurate shape sensing of continuum robots," in Proceedings—IEEE International Conference on Robotics and Automation. Institute of Electrical and Electronics Engineers Inc., 2014, pp. 5374-5379.

Chunwoo Kim, S. C. Ryu, and P. E. Dupont, "Real-time adaptive kinematic model estimation of concentric tube robots," in 2015 IEEE/RSJ International Conference on Intelligent Robots and Systems (IROS). IEEE, Sep. 2015, pp. 3214-3219.

A. Brij Koolwal, F. Barbagli, C. Carlson, and D. Liang, "An Ultrasound-based Localization Algorithm for Catheter Ablation Guidance in the Left Atrium," The International Journal of Robotics Research, vol. 29, No. 6, pp. 643-665, May 2010.

A. W. Mahoney, T. L. Bruns, P. J. Swaney, and R. J. Webster, "On the inseparable nature of sensor selection, sensor placement, and state estimation for continuum robots or where to put your sensors and how to use them," in 2016 IEEE International Conference on Robotics and Automation (ICRA). IEEE, May 2016, pp. 4472-4478.

Messenger JC, Ho KKL, Young CH et al. and NCDR Science and Quality Oversight Committee Data Quality Workgroup, "The National Cardiovascular Data Registry (NCDR) Data Quality Brief: The NCDR Data Quality Program in 2012." Journal of the American College of Cardiology. (2012); 60(16):1484-1488.

D. E. Ost, et al., "Diagnostic Yield and Complications of Bronchoscopy for Peripheral Lung Lesions. Results of the AQuIRE Registry," American Journal of Respiratory and Critical Care Medicine, vol. 193, No. 1, pp. 68-77, Jan. 2016.

J. Rosell, A. Perez, P. Cabras, and A. Rosell, "Motion planning for the Virtual Bronchoscopy," in 2012 IEEE International Conference on Robotics and Automation. IEEE, May 2012, pp. 2932-2937.

Saver JL, Goyal M, van der Lugt A, et al., "Time to treatment with endovascular thrombectomy and outcomes from ischemic stroke: a meta-analysis." JAMA (2016) 316(12):1279-1288.

Sganga, Jake, et al. "Autonomous Driving in the Lung using Deep Learning for Localization." Main Paper. Jul. 16, 2019; pp. 1-10.

Sganga, Jake, et al. "OffsetNet: Deep Learning for Localization in the Lung using Rendered Images." Stanford Education; Sep. 15, 2018. pp. 1-7.

Sganga, Jake, et al. "Orientation Estimation of a Continuum Manipulator in a Phantom Lung." Stanford Education; pp. 1-7.

O. K. Bruno Siciliano, Handbook of Robotics, 2008, Springer, vol. 53, No. 9. TOC.

S. Tully and H. Choset, "A Filtering Approach for Image-Guided Surgery with a Highly Articulated Surgical Snake Robot," IEEE Transactions on Biomedical Engineering, vol. 63, No. 2, pp. 392-402, Feb. 2016.

Venema E, Groot AE, Lingsma HF, et al., 'Effect of interhospital transfer on endovascular treatment for acute ischemic stroke' (2019); pp. 1-8.

Walker. "Continuous Backbone "Continuum" Robot Manipulators." ISRN Robotics. Hindawi Publishing Corporation. vol. 2013, Article ID 726506, 19 pages.

E. Wan and R. Van Der Merwe, "The unscented Kalman filter for nonlinear estimation," in Proceedings of the IEEE 2000 Adaptive Systems for Signal Processing, Communications, and Control Symposium (Cat. No. 00EX373). IEEE, pp. 153-158.

R. J. Webster and B. A. Jones, "Design and Kinematic Modeling of Constant Curvature Continuum Robots: A Review," The International Journal of Robotics Research, vol. 29, No. 13, pp. 1661-1683, Nov. 2010.

R. Xu, A. Yurkewich, and R. V. Patel, "Curvature, Torsion, and Force Sensing in Continuum Robots Using Helically Wrapped FBG Sensors," IEEE Robotics and Automation Letters, vol. 1, No. 2, pp. 1052-1059, Jul. 2016.

R. Xu, A. Yurkewich, and R. V. Patel, "Shape sensing for torsionally compliant concentric-tube robots," in SPIE BiOS, I. Gannot, Ed. International Society for Optics and Photonics, Mar. 2016, Proc. of SPIE vol. 9702, 97020V. 9 pages.

Yang et al., Deep Learning Segmentation of Major Vessels in X-Ray Coronary Angiography, Scientific Reports (2019); pp. 1-11.

M. Yip and D. Camarillo, "Model-Less Feedback Control of Continuum Manipulators in Constrained Environments," IEEE Transactions on Robotics, vol. 30, No. 4, pp. 880-889, Aug. 2014.

International Search Report for International Application No. PCT/US2022/035848 dated Aug. 12, 2022.

International Search Report for International Application No. PCT/US2022/040118 dated Nov. 22, 2022.

Buther F, Dawood M, Stegger L, Wubbeling F, Schafers M, Schober O, Schafers KP. List mode-driven cardiac and respiratory gating in PET. J Nucl Med. 2009;50(5):674-81. Epub Apr. 18, 2009. doi: 10.2967/jnumed.108.059204. PubMed PMID: 19372491.

(56) References Cited

OTHER PUBLICATIONS

Desjardins B, Kazerooni EA. ECG-gated cardiac CT. AJR Am J Roentgenol. 2004;182(4):993-1010. Epub Mar. 25, 2004. doi: 10.2214/ajr.182.4.1820993. PubMed PMID: 15039178.

Fallavollita P. Is single-view fluoroscopy sufficient in guiding cardiac ablation procedures? Int J Biomed Imaging. 2010;2010:631264. doi: 10.1155/2010/631264. PubMed PMID: 20368770; PMCID: PMC2846336.

Jang S-J, Torabinia M, Dhrif H, Caprio A, Liu J, Wong SC, Mosadegh B. Development of a Hybrid Training Simulator for Structural Heart Disease Interventions. Advanced Intelligent Systems. 2020;2(12):2000109.

Koivumaki T, Nekolla SG, Furst S, Loher S, Vauhkonen M, Schwaiger M, Hakulinen MA. An integrated bioimpedance—ECG gating technique for respiratory and cardiac motion compensation in cardiac PET. Phys Med Biol. 2014;59(21):6373-85. Epub Oct. 9, 2014. doi: 10.1088/0031-9155/59/21/6373. PubMed PMID: 25295531.

Liu J, AF Aref SJ, Singh G, Caprio A, Moghadam AAA, Jang S-J, Wong SC, Min JK, Dunham S, Mosadegh B. An augmented reality system for image guidance of transcatheter procedures for structural heart disease. PLOS One. 2019:14(7):e0219174. doi: 10.1371/journal.pone.0219174.

Ronneberger O, Fischer P, Brox T, editors. U-net: Convolutional networks for biomedical image segmentation. International Conference on Medical image computing and computer-assisted intervention; 2015: Springer.

Sra J, Krum D, Choudhuri I, Belanger B, Palma M, Brodnick D, Rowe DB. Identifying the third dimension in 2D fluoroscopy to create 3D cardiac maps. JCI Insight. 2016;I(21):e90453. doi: 10.1172/jci.insight.90453. PubMed PMID: 28018976; PMCID: PMC5 161213.

Torabinia, M., Caprio, A., Jang, S. J., Ma, T., Tran, H., Mekki, L., & Mosadegh, B. (2021). Deep learning-driven catheter tracking from bi-plane X-ray fluoroscopy of 3D printed heart phantoms. Mini-invasive Surgery, 5.

\* cited by examiner

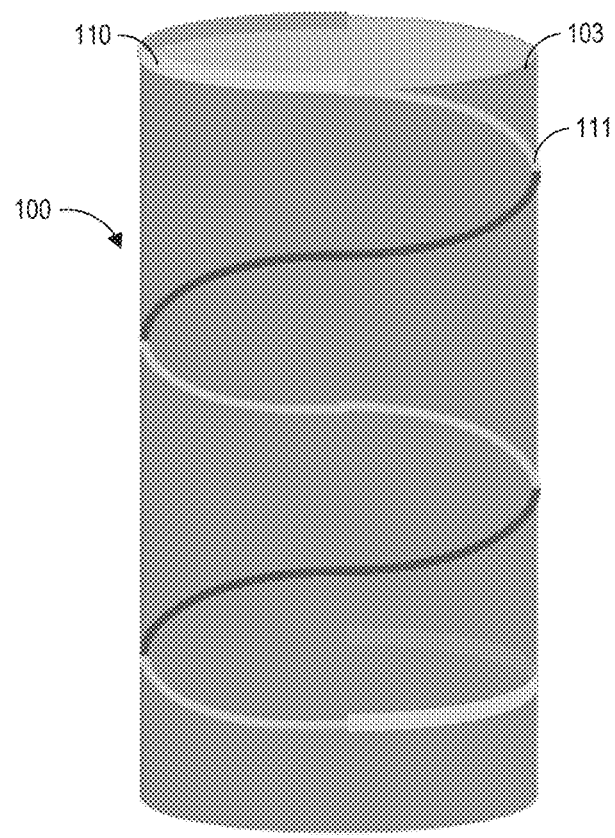
FIG. 7A
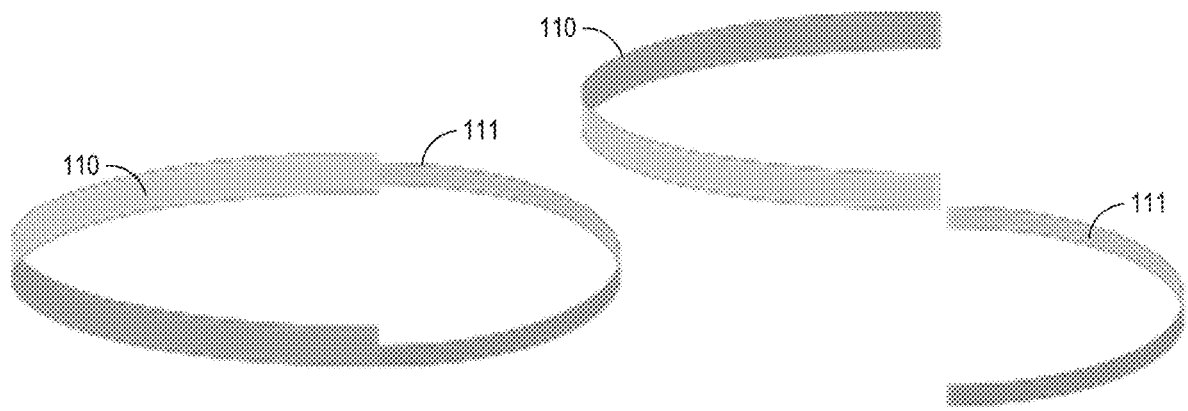
FIG. 7B  FIG. 7C

FIG. 8C

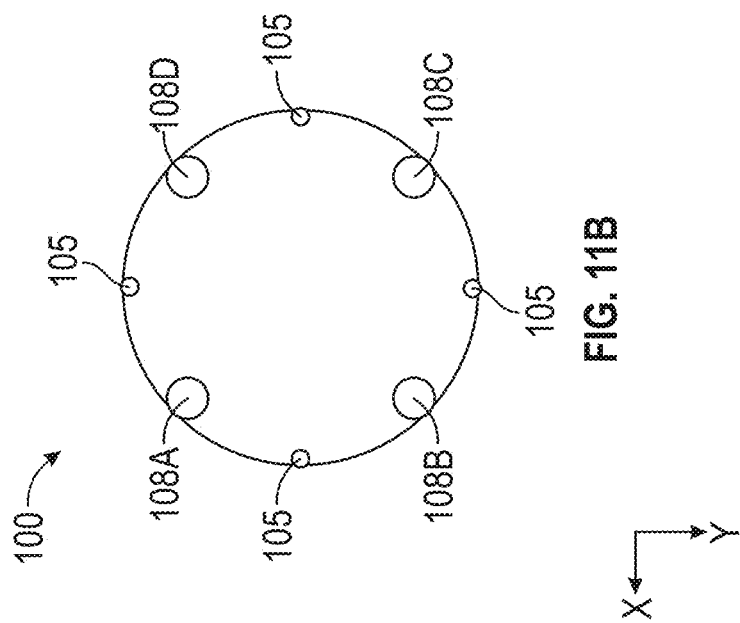
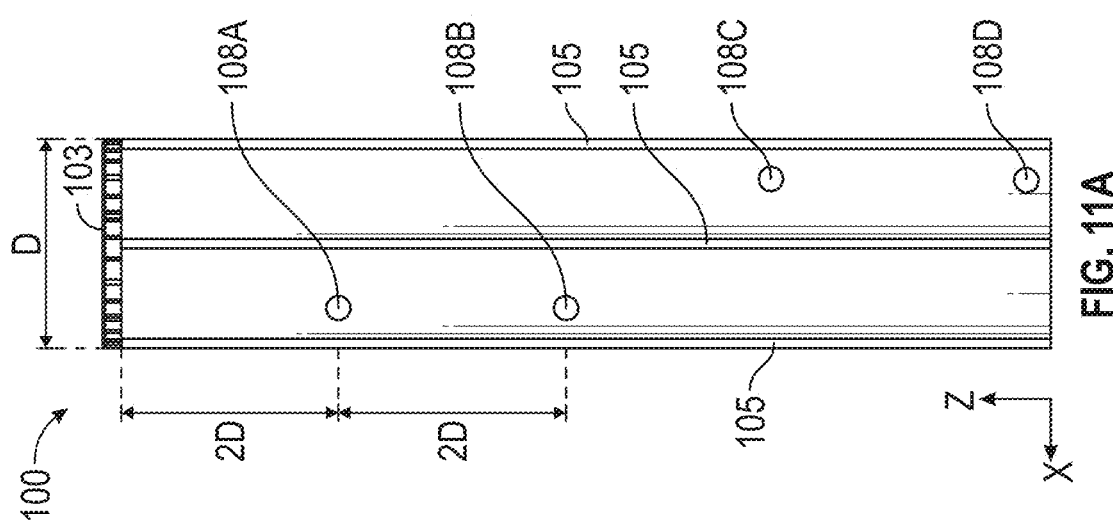

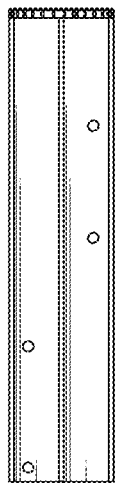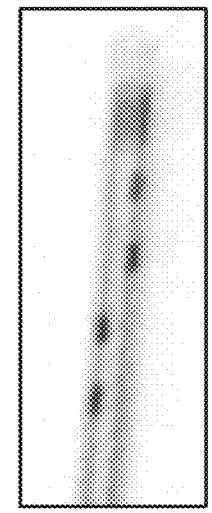
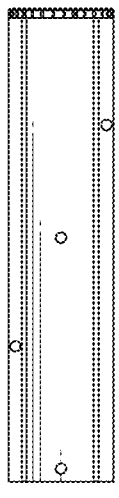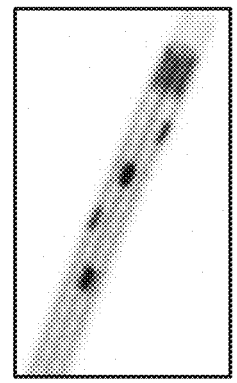
FIG. 12A　　　　　　　　FIG. 12B
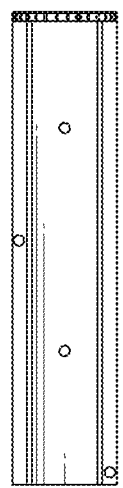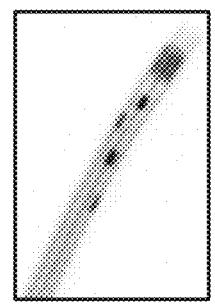
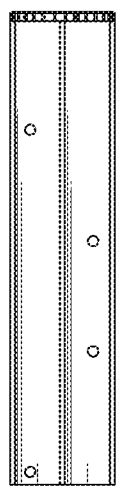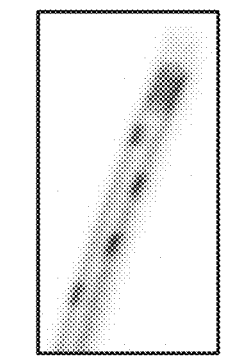
FIG. 12C　　　　　　　　FIG. 12D

VISION-BASED POSITION AND ORIENTATION DETERMINATION FOR ENDOVASCULAR TOOLS

PRIORITY APPLICATIONS

This application claims priority to U.S. Provisional Application No. 63/202,963, filed Jul. 1, 2021, and to U.S. Provisional Application No. 63/264,531, filed Nov. 24, 2021, each of which are incorporated herein by reference. Any and all applications for which a foreign or domestic priority claim is identified in the Application Data Sheet as filed with the present application are hereby incorporated by reference under 37 CFR 1.57.

BACKGROUND

Field

The present application is directed to vision-based position and/or orientation determination for endovascular and other intraluminal tools or medical instruments, such as catheters. In some embodiments, the devices, systems, and methods described herein can be included in or used in conjunction with robotic medical systems configured to facilitate control and operation of the medical instrument.

Description

Endovascular medical procedures are common. During an endovascular procedure, a tool or medical instrument that is generally configured as a long, thin, flexible body is inserted into and navigated through a lumen or other cavity of the body.

In some instances, the tools or medical instruments are articulable or controllable, for example, using one or more pull wires, to allow an operator to navigate the tool or medical instrument within the body. Such navigation is often accomplished through deflection (for example, bending) of the distal tip of the tool or medical instrument.

Some tools or medical instruments are configured for manual control, for example, using knobs or levers mounted on a proximally-located handle of the tool or medical instrument. In other instances, the tools or medical instruments can be configured for robotic control, for example, control by a robotic medical system. In some embodiments, an operator can use the robotic medical system (for example, a controller, user interface, and/or the like) to robotically control the tool or medical instrument.

SUMMARY

This application describes devices, systems, and methods for detecting or determining position and/or orientation of endovascular or other intraluminal tools or medical instruments, such as catheters. The determination of position and orientation can be made based on a two-dimensional medical image, such as a single plane X-ray image. For example, computer vision can be used to analyze a two-dimensional medical image to determine the position and/or orientation of the catheter based on radio-opaque markers that are included on the catheter. In some instances, five degrees of freedom for the catheter can be determined: two positional degrees of freedom (e.g., x and y position) and three degrees of freedom relating to orientation (e.g., heading, incline, and roll). Various example configurations for the radio-opaque markers are disclosed. The use of other configurations for the radio-opaque markers is also possible, and this disclosure should not be limited to only the disclosed configurations.

The devices, systems, and methods described herein can provide several notable advantages over existing technologies. For example, position and orientation can be determined using minimally sophisticated medical imaging (e.g., single plane X-ray). Suitable medical imaging devices are widely available, allowing the devices, systems, and methods described herein to be widely available. Additionally, position and orientation can be determined without the additional hardware that is often required by other systems. For example, existing systems often determine position and orientation using electromagnetic sensors and electromagnetic field generators. Such systems are cumbersome and relatively inaccurate, requiring precise registrations with other forms of data (e.g., medical imaging data, computer models, robotic movement data, etc.) in order to be useful. With the principals described herein, the need for such systems can be avoided. Finally, the devices, systems, and methods of the present application can allow for safer and more precise control of a catheter. This can, in turn, facilitate remote or autonomous control of the catheter. These and other benefits and advantages of the application will become more apparent after considering the disclosure and drawings in the Detailed Description section below.

In a first aspect, a computer-implemented system comprises at least one processor and at least one electronic storage medium, the electronic storage medium storing instructions configured to cause the at least one processor to: receive, from a medical imaging device, a two-dimensional medical image including a view of at least a distal portion of a medical instrument, the distal portion of the medical instrument including one or more fiducials positioned thereon, the one or more fiducials being radio-opaque and visible in the medical image; detect, within the medical image, a two-dimensional appearance of the one or more fiducials; and based on the two-dimensional appearance of the one or more fiducials, determine at least one of: a roll angle of the distal portion of the medical instrument, and an incline of the distal portion of the medical instrument.

The system may include one or more of the following features in any combination: (a) wherein the at least one processor is configured to detect the two-dimensional appearance of the one or more fiducials based on a computer vision algorithm; (b) the at least one processor is configured to detect the two-dimensional appearance of the one or more fiducials using a neural network; (c) wherein the at least one processor is further configured to determine both of the roll angle of the distal portion of the medical instrument and the incline of the distal portion of the medical instrument; (d) wherein the at least one processor is further configured to determine the incline with respect to an image plane of the two-dimensional medical image; (e) wherein the one or more fiducials are configured such that the two-dimensional appearance of the fiducials within the medical image is visually distinguishable for different roll angles and different inclines of the medical instrument; (f) wherein the one or more fiducials are configured such that the two-dimensional appearance of the fiducials within the medical image is visually distinguishable for different roll angles and different inclines of the medical instrument for incremental changes of less than 5 degrees, less than 10 degrees, less than 15 degrees, less than 20 degrees, less than 25 degrees, less than 30 degrees, less than 35 degrees, or less than 40 degrees; (g) wherein the one or more fiducials are configured such that the two-dimensional appearance of the fiducials within the medical image is visually distinguishable for different roll angles and different inclines of the medical instrument for incremental changes of about 5 degrees, about 10 degrees, about 15 degrees, about 20 degrees, about 25 degrees, about 30 degrees, about 35 degrees, or about 40 degrees; (h) wherein the at least one processor is further configured to detect, within the medical image, a distal tip of the medical instrument, and based on the detected distal tip of the medical instrument, determine a two-dimensional position of the distal tip of the medical instrument within a plane of the two-dimensional medical image; (i) wherein detecting the distal tip of the medical instrument comprises determining, based on the medical image, a centerline of the distal portion of the medical instrument, and determining an endpoint for the centerline; (j) wherein the at least one processor is further configured to detect, within the medical image, a portion of the medical instrument, and based on the detected distal portion of the medical instrument, determine a heading of the medical instrument within a plane of the two-dimensional medical image; (k) wherein determining the heading of the medical instrument comprises determining, based on the medical image, a centerline of the distal portion of the medical instrument, and determining an endpoint for the centerline, and determining a vector extending from the endpoint, the vector being colinear with a distal portion of the centerline; (l) wherein the medical instrument comprises an endoluminal medical instrument; (m) wherein the medical instrument comprises a catheter; (n) wherein the medical imaging device comprises an X-ray device; (o) wherein the processor is further configured to determine one or more motor controls configured to cause articulation of the distal portion of the medical instrument, wherein the one or more motor controls are determined at least in part based on the determined roll angle or the determined incline, and transmit the one or more motor controls to a robotic system coupled with the medical instrument, whereby the robotic system causes articulation of the medical instrument based on the one or more motor controls; (p) wherein the processor is further configured to determine the one or more motor controls based on a user input; (q) wherein the processor is further configured to cause the determined roll angle or the determined incline to be displayed on a user display; (r) the processor is further configured to cause the two-dimensional medical image to be displayed on the user display; and/or other features as described throughout this application.

In another aspect, a method includes: receiving, from a medical imaging device, a two-dimensional medical image including a view of at least a distal portion of a medical instrument, the distal portion of the medical instrument including one or more fiducials positioned thereon, the one or more fiducials being radio-opaque and visible in the medical image; detecting, within the medical image, a two-dimensional appearance of the one or more fiducials; and based on the two-dimensional appearance of the one or more fiducials, determining at least one of: a roll angle of the distal portion of the medical instrument, and an incline of the distal portion of the medical instrument.

The method may include one or more of the following features in any combination: (a) wherein detecting the two-dimensional appearance of the one or more fiducials is based on a computer vision algorithm; (b) detecting the two-dimensional appearance of the one or more fiducials using a neural network; (c) determining both of the roll angle of the distal portion of the medical instrument and the incline of the distal portion of the medical instrument; (d) determining the incline with respect to an image plane of the two-dimensional medical image; (r) wherein the one or more fiducials are configured such that the two-dimensional appearance of the fiducials within the medical image is visually distinguishable for different roll angles and different inclines of the medical instrument; (f) wherein the one or more fiducials are configured such that the two-dimensional appearance of the fiducials within the medical image is visually distinguishable for different roll angles and different inclines of the medical instrument for incremental changes of less than 5 degrees, less than 10 degrees, less than 15 degrees, less than 20 degrees, less than 25 degrees, less than 30 degrees, less than 35 degrees, or less than 40 degrees; (g) wherein the one or more fiducials are configured such that the two-dimensional appearance of the fiducials within the medical image is visually distinguishable for different roll angles and different inclines of the medical instrument for incremental changes of about 5 degrees, about 10 degrees, about 15 degrees, about 20 degrees, about 25 degrees, about 30 degrees, about 35 degrees, or about 40 degrees; (h) detecting, within the medical image, a distal tip of the medical instrument, and based on the detected distal tip of the medical instrument, determining a two-dimensional position of the distal tip of the medical instrument within a plane of the two-dimensional medical image; (i) wherein detecting the distal tip of the medical instrument comprises determining, based on the medical image, a centerline of the distal portion of the medical instrument, and determining an endpoint for the centerline; (j) detecting, within the medical image, a portion of the medical instrument, and based on the detected distal portion of the medical instrument, determine a heading of the medical instrument within a plane of the two-dimensional medical image; (k) wherein determining the heading of the medical instrument comprises determining, based on the medical image, a centerline of the distal portion of the medical instrument, and determining an endpoint for the centerline, and determining a vector extending from the endpoint, the vector being colinear with a distal portion of the centerline; (l) wherein the medical instrument comprises an endoluminal medical instrument; (m) wherein the medical instrument comprises a catheter; (n) wherein the medical imaging device comprises an X-ray device; (o) determining one or more motor controls configured to cause articulation of the distal portion of the medical instrument, wherein the one or more motor controls are determined at least in part based on the determined roll angle or the determined incline, and transmitting the one or more motor controls to a robotic system coupled with the medical instrument, whereby the robotic system causes articulation of the medical instrument based on the one or more motor controls; (p) determining the one or more motor controls based on a user input; (q) causing the determined roll angle or the determined incline to be displayed on a user display; ® causing the two-dimensional medical image to be displayed on the user display; and/or other features as described throughout this application.

For purposes of this summary, certain aspects, advantages, and novel features are described herein. It is to be understood that not necessarily all such advantages may be achieved in accordance with any particular embodiment. Thus, for example, those skilled in the art will recognize the disclosures herein may be embodied or carried out in a manner that achieves one or more advantages taught herein without necessarily achieving other advantages as may be taught or suggested herein.

All of the embodiments described herein are intended to be within the scope of the present disclosure. These and other embodiments will be readily apparent to those skilled in the art from the following detailed description, having reference to the attached figures. The invention is not intended to be limited to any particular disclosed embodiment or embodiments.

BRIEF DESCRIPTION OF THE DRAWINGS

These and other features, aspects and advantages of the present application are described with reference to drawings of certain embodiments, which are intended to illustrate, but not to limit, the present disclosure. It is to be understood that the attached drawings are for the purpose of illustrating concepts disclosed in the present application and may not be to scale.

FIGS. 7A-7C illustrate an example of a semicircular marker for a catheter configured to allow for, among other things, determination of the sign of the incline of the catheter.

FIG. 8C illustrates example two-dimensional appearances of radio-opaque markers at various heading and roll positions.

FIGS. 11A and 11B are side and top views of an embodiment of a catheter that includes markers configured to allow for determination of, among other things, a catheter roll angle.

FIGS. 12A-12D show the catheter and markers at various roll positions.

DETAILED DESCRIPTION

Figure 1A:
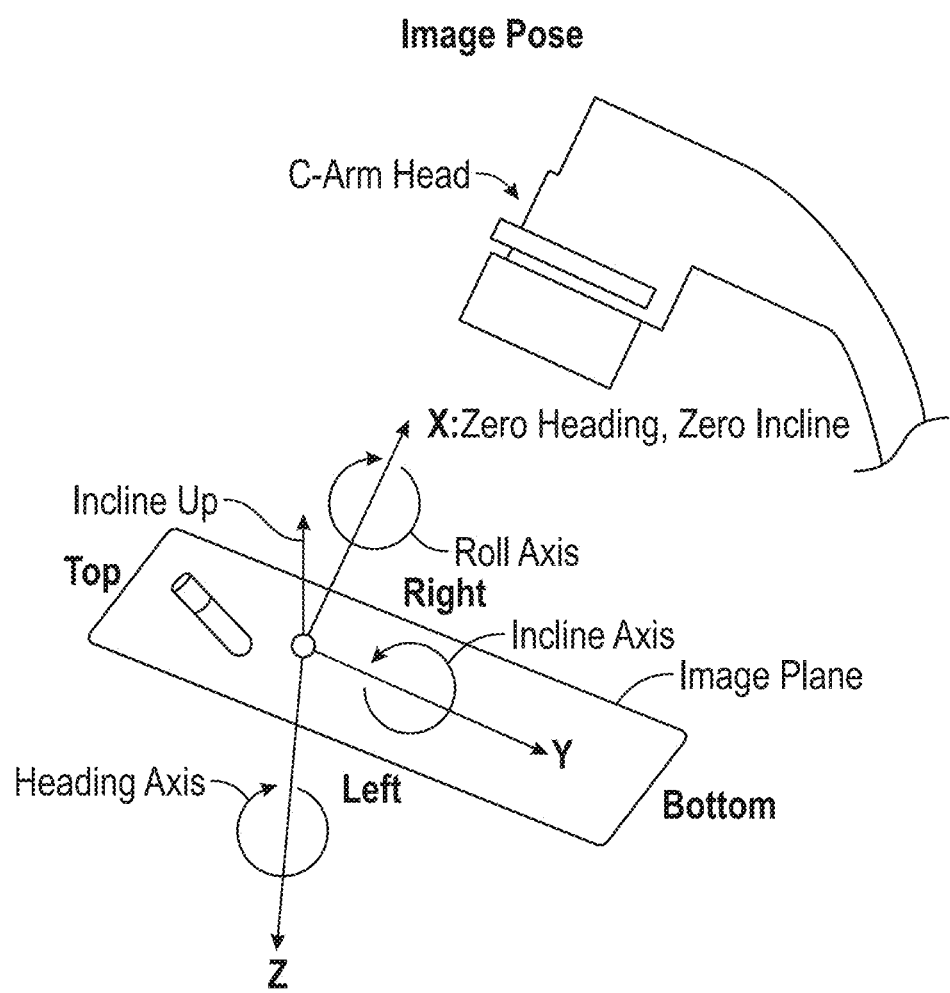
FIGS. 1A-1E illustrate an example coordinate system for three-dimensional image pose estimation.

This application describes devices, systems, and methods for detecting or determining the position and/or orientation of endovascular or other intraluminal tools or medical instruments, such as catheters. In some instances, the term "pose" is used herein to refer to the position and orientation of a catheter. In some embodiments, determination of pose can be made based on a two-dimensional medical image, such as a single plane X-ray image, and one or more radio-opaque markers included on a catheter. Computer vision models can be employed to detect the radio-opaque markers in the two-dimensional medical image and to determine the pose of the catheter therefrom. In some instances, the pose can be defined by five degrees of freedom for the catheter. The five degrees of freedom can include two positional degrees of freedom (e.g., x and y position) and three degrees of freedom relating to orientation (e.g., heading, incline, and roll). In other embodiments, the pose can comprise greater (e.g., six) or fewer (e.g., four or fewer) degrees of freedom. The pose of an instrument can be defined in many different ways. While this application primarily describes examples of pose in terms of x, y, and z for position, and heading, incline, and roll for orientation, other methods for describing or defining the pose (e.g., alternative coordinate systems, alternative naming conventions, etc.) are possible, and the principles of this application extend to all methods for defining pose. Further, in some embodiments, the methods and systems of this application may be used to determine one, more than one, or all elements of pose.

The principals described herein can be applicable to robotic medical procedures, for example, where the catheter is robotically controlled by a robotic medical system that is configured to insert, retract, roll, and/or articulate the catheter based on inputs received from a physician or in an autonomous or semi-autonomous manner. In some instances the principals of this disclosure may also be applicable to manually controlled catheters.

The principles of this disclosure are described below with primary reference to examples wherein the medical instrument or tool is an endovascular catheter configured to navigate within the vasculature of the patient. These examples, however, should not be construed as limiting of the principles of the disclosure. Those of skill in the art, upon consideration of the principles disclosed herein, will appreciate that the devices, systems, and methods for detecting or determining position and/or orientation described herein have application in other contexts. For examples, the principles described herein can be useful with other endoluminal, endoscopic, or laparoscopic tools, instruments, procedures and/or the like. For ease of illustration, however, a primary example related to an endovascular catheter is provided. Accordingly, it should be realized that any of the following description of an endovascular catheter or catheter may also be applied to other endoluminal, endoscopic, and/or laparoscopic tools or the like. Additionally, it should be realized that while this application provides several example configurations for tools or medical instruments that include specific configurations of radio-opaque markers, other configurations of radio-opaque markers can also be used.

Safe navigation of a catheter within a patient's body generally requires an accurate understanding of the current pose of the catheter. It can be difficult to gain an accurate understanding of pose from a single two-dimensional medical image. For example, FIG. 2B provides an example X-ray image of a catheter 100 navigating through an aortic arch of a patient. From FIG. 2B alone, however, a person would have difficulty understanding the exact pose of the catheter 100. For example, does the catheter 100 lie completely within the plane of the image, or is it inclined into or out of the plane of the image? Highly skilled physicians may be able to make educated guesses with respect to these questions based on their understanding of human anatomy. Still, however, uncertainty exists, which increases the risk of damage to the patient during a medical procedure.

Perhaps even more critically, from FIG. 2B alone, it is extremely difficult, if not impossible, for even skilled physicians to determine the current roll angle of the catheter 100 (i.e., the rotational angle of the catheter about its longitudinal axis). Understanding the current roll of the catheter 100 can be critical for safe navigation, especially considering how most articulable catheters are controlled. Most articulable catheters include pullwires that can be actuated (e.g., tensioned or pulled) to cause deflection of a distal tip of the catheter. See, for example, the catheter 100 of FIG. 2A described below. Commonly, catheters include four pullwires, each configured to cause deflection of the catheter in one of four cardinal directions. For example, one pullwire can be associated with deflecting the tip of the catheter up, one pullwire can be associated with deflecting the tip down, one pullwire can be associated with deflecting the tip right, and one pullwire can be associated with deflecting the tip down. However, in order to know which pullwire to actuate to cause a given deflection requires an understanding of the current roll position of the catheter. For example, if the distal tip of the catheter is rolled by 90 degrees, actuating the pullwire generally associated with an upward deflection of the tip would instead cause the catheter to articulate (possibly unexpectedly) to the right or left. Unintended articulation can frustrate navigation and cause injury to a patient. Moreover, the distal tip of a catheter often rolls (in unexpected ways) as the catheter is navigated through complex anatomy, such as through a vascular network of a patient, even if roll inputs are not provided at the proximal (e.g., external) end of the catheter.

As will be described in more detail below, the systems, methods, and devices provide for accurate determination of the pose of a catheter (including its roll) based on detection of radio-opaque fiducials included on the catheter. In some embodiments, detection of the radio-opaque fiducials is achieved using computer vision analysis of a two-dimensional medical image of the catheter. The methods and systems described herein can also be used with biplane imaging systems to determine six degree of freedom pose estimates of the catheter. In such cases, determination of incline may (in some instances) be determined from the biplane images, while roll angle can be determined based on computer vision analysis of the radio-opaque fiducials included on the catheter.

FIGS. 1A-1E illustrate an example coordinate system for three-dimensional image pose estimation or determination. As noted above, the term "pose" is used herein to refer to the different combinations of positions and/or orientations of an endovascular tool, intraluminal tool, medical instrument and/or the like. Position can refer to, for example, an x, y, and z position (for example, a location within three-dimensional space). In some embodiments, position can refer to the x and y position within the two-dimensional image plane of a medical image, such as an X-ray. Orientation can be represented in many different ways. In general, in this application, orientation is referred to using three Euler angles: (1) heading, which can be a measure of angulation or articulation about the z-axis and/or where the device is pointing in the image plane; (2) incline, which can be a measure of rotation about the x-axis and/or where the device is pointing out of the image plane (e.g., pitch); and (3) roll which can be a measure of rotation about the longitudinal or central axis of the catheter.

Figure 1B:
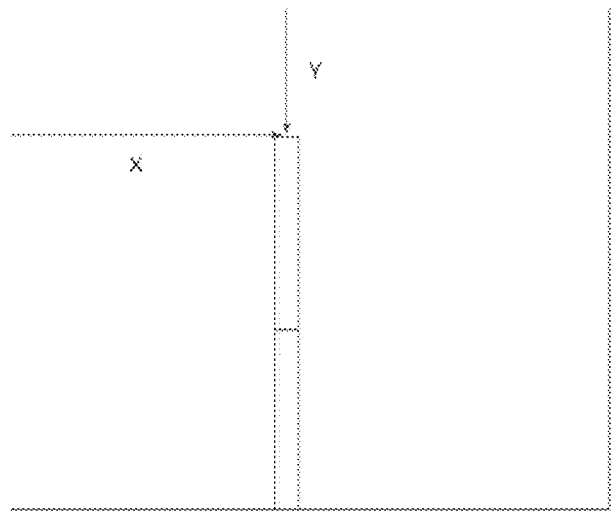
Figure 1C:
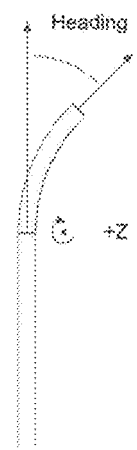
Figure 1D:
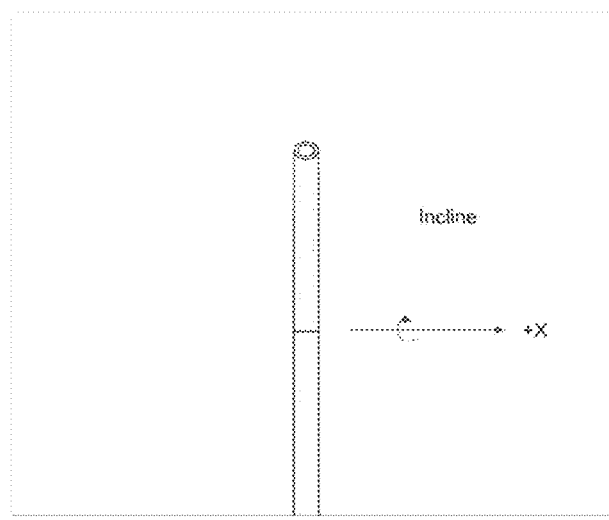
Figure 1E:

FIG. 1A is a perspective schematic view of the example coordinate system. As shown, a medical imager, illustrated as a C-arm head, is positioned and configured to capture a medical image within a two-dimensional image plane, which in the illustrated example, corresponds to the x-y plane (in which the two-dimensional x and x position of the catheter can be determined). Orientation of the catheter can be defined with respect to heading, incline, and roll as shown. FIGS. 1B-1E provide additional illustrations. FIG. 1B represents two-dimensional position within the x-y plane of the medical image. FIG. 1C illustrates the heading angle, measured about the z-axis, which generally corresponds to the apparent heading or direction of the catheter within the x-y plane of the image. FIG. 1D illustrates the incline angle, measured about the x-axis, which generally corresponds to a measurement of the angle into or out of the plane of the image. FIG. 1E illustrates the roll of the catheter, measured about the catheter's longitudinal or central axis. The methods and systems described herein are also applicable to determination of one, more than one, or all elements of pose, regardless of the manner in which pose is defined (e.g., regardless of coordinate system, nomenclature, etc.).

As will be further described herein, the use of computer vision algorithms and unique radio-opaque markings or fiducials can be included on the catheter that may be used to quantitatively estimate the endovascular tool's five-dimensional pose (for example, two-dimensional position (e.g., see FIG. 1B), as well as its heading (e.g., FIG. 1C), incline (e.g., FIG. 1D), and roll (e.g., FIG. 1E)). The use of radio-opaque markings can preserve the readily visible dimensions, for example, the position of the endovascular tool on the image plane (the x and y position) and the direction the endovascular tool points in the image plane (the heading), and further, the use of unique radio-opaque markings can further allow the sign of the incline dimension, the degree of incline dimension, and the roll to be quantitatively estimated or determined. While many different radio-opaque materials may be used, in some embodiments, it may be preferable to use platinum, tungsten, and/or gold because of their superior X-ray attenuation properties. In some embodiments, the radio-opaque material may be a piece of wire, metal, radio-opaque ink and/or the like that is place within a layer of the catheter or other tool. Examples are provided below.

Figure 2A:
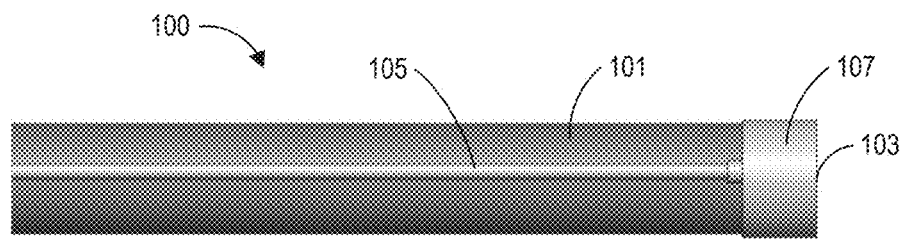
FIG. 2A illustrates a side view of a distal end of an embodiment of an endovascular catheter.
Figure 2B:
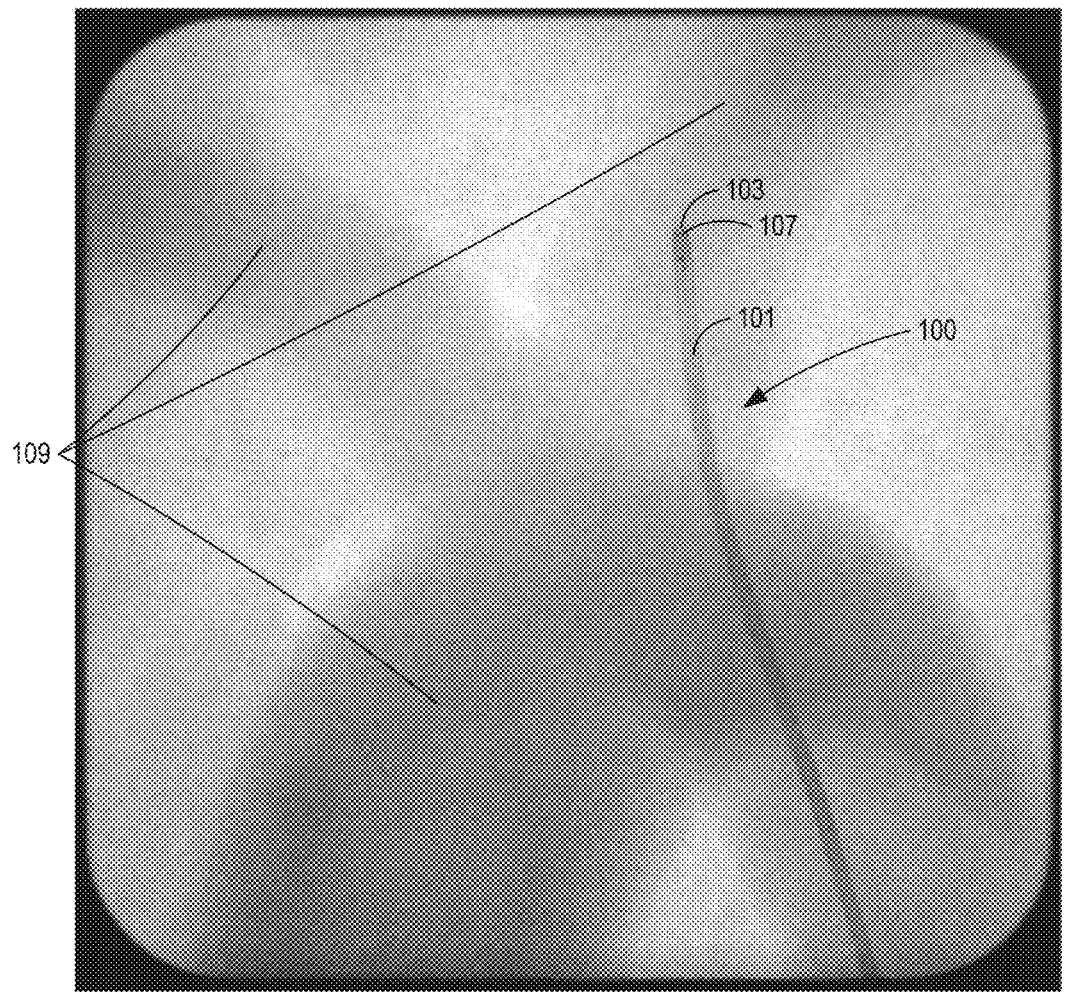
FIG. 2B is a fluoroscopic image illustrating an endovascular catheter, such as that shown in FIG. 2A, navigating through a vascular network of a patient, according to an embodiment.

FIG. 2A illustrates a distal end of an embodiment of an endovascular catheter 100. In the illustrated embodiment, the catheter 100 includes a long, thin, and flexible body 101 that extends to a distal end 103. The body 101 can be configured to be navigated through the patient's vasculature. In some embodiments, a channel may be formed through the body 101 such that other tools or instruments can be passed through the catheter 100 and gain access to the patient's anatomy through an opening that can be included on the distal end 103 of the catheter. In some embodiments, one or more tools can be integrated directly into the catheter 100 itself.

To facilitate navigation, in some embodiments (such as the illustrated embodiment of FIG. 2A), the catheter 100 or a distal portion thereof can be configured to be articulable or deflectable. To achieve articulation, the catheter 100 includes one or more pull wires 105 that extend on, in, or through the body 101 and attach at or near the distal end 103. Actuation (e.g., pulling or shortening) the pull wires 105 at or near their proximal end can be configured to cause a distal portion of the catheter 100 to deflect or articulate. Depending on the number and arrangement of pull wires 105, the catheter 100 can be configured for one-way, two-way, three-way, or four-way deflection, although other configurations providing different degrees of articulation or deflection are also possible.

The catheter 100 can be configured such that control thereof (e.g., control of the deflection of the distal portion of the catheter 100) can be accomplished manually or robotically. For example, in some embodiments that are configured for manual control, the body 101 and pull wires 105 extend proximally to a handle located on a proximal end of the catheter 100 (not shown). The handle can be configured to by operated by hand (e.g., manually) to actuate the pull wires 105. For example, the handle can include one or more manual inputs such as levers, buttons, dials and/or the like that allow a user to manually actuate the pull wires 105 to cause deflection of the distal portion of the catheter 100. In some robotically controllable embodiments, the body 101 and pull wires 105 extend proximally to a base located on a proximal end of the catheter 100 (not shown). The base can be configured to connect to and be operated by a robotic medical system to actuate the pull wires 105. For example, the base can include one or more robotic inputs configured to engage with robotic outputs or actuators on the robotic medical system. In some embodiments, other methods and configurations for manual and robotic control may be used.

FIG. 2A also illustrates that, in some embodiments, the catheter 100 can include a marker (or fiducial) 107. In the illustrated embodiment, the marker 107 is positioned at the distal end 103 of the catheter 100. The marker 107 can be configured to facilitate identification of the distal end 103 of the catheter 100 in a medical image captured during a medical procedure. For example, the marker 107 can be radio-opaque so as to be readily identifiable within a fluoroscopic image. In some embodiments, the marker 107 comprises a radio-opaque ring positioned on the distal end 103 of the catheter 100. When the marker 107 comprises a radio-opaque material, it can be more easily identified within, for example, a fluoroscopic image such as an X-ray. Identification of the distal end 103 within a medical image during a procedure can greatly facilitate navigation and control of the catheter 100.

FIG. 2B provides an example medical image of a catheter 100, such as the catheter 100 of FIG. 2A, navigating within the vasculature of the patient. In particular, the image of FIG. 2B is a fluoroscopic X-ray image. As shown, both blood vessels 109 of the patient's vasculature, as well as the catheter 100 itself, are visible in the image. The marker 107 included at the distal end 103 of the catheter 100 helps a user (or a computer-vision algorithm) viewing the image to identify the distal end 103 of the catheter 100. Because the marker 107 comprises a radio-opaque material, it shows up well within the image.

In general, during an endovascular procedure, a physician or other operator, attempts to guide the distal end 103 of the catheter 100 to a specific location, such as, for example a treatment site. For example, one such procedure is a mechanical thrombectomy. A large vessel occlusion (LVO) stroke occurs when a blood clot lodges in at least one of the internal carotid, proximal middle cerebral artery, proximal anterior cerebral artery, basilar artery, or vertebral artery. Such a clot can partially or completely occlude downstream blood supply to brain tissue resulting in neuronal infarction and subsequent neurological impairment or death. During a mechanical thrombectomy, a physician gains access to the patient's vasculature and inserts a catheter, such as catheter 100. The catheter 100 is guided to the obstruction using, for example, one or more medical images similar to the one shown in FIG. 2B. Once the distal end 103 of the catheter 100 is positioned near the obstruction, tools are passed through the working channel of the catheter 100 to remove the obstruction.

While medical images, such as that shown in FIG. 2B, may help the physician guide the catheter 100 to the treatment site, it is still difficult to fully determine the orientation or pose of the catheter 100 from the medical image alone. This occurs, for example and among other reasons, because the medical image often provides only a two-dimensional view of the patient's anatomy (e.g., the vasculature) and the catheter 100, each of which, in actuality, comprise three-dimensional shapes. In the past (for example, without the systems, methods, and devices described herein), physicians needed to rely on their knowledge of anatomy as well as various other assumptions (such as an assumption that the catheter 100 is located within the vasculature) to interpret the two-dimensional medical image in a three-dimensional way. While many specialists are able to do this to a limited extent, this can provide a barrier to the availability of such procedures. Further, because different patients have different anatomies, the results are not always precise.

Considering FIG. 2B, for example, one can relatively easily understand the shape of the catheter 100 within the plane of the two-dimensional of the image. However, the shape of the catheter 100 out of the plane of the image (e.g., the incline of the catheter) is harder to discern. For example, in FIG. 2B, it is difficult to determine whether the catheter 100 is moving in a direction that is into or out of the plane of the image. While an understanding of anatomy can inform the answer to this question, the result is still not wholly determinable. As will be described in more detail below, this application offers new devices, systems, and methods for determining an out of the plane angle of the distal end 103 of the catheter 100. Increasing a physician's understanding of the out of the plane angle of the distal end 103 of the catheter 100 can greatly facilitate navigation and improve the experience of driving or controlling the catheter 100.

As described above, the catheter 100 may include an articulable portion that is actuated via pull wires. To accurately control the articulation of the catheter 100, one must understand the roll orientation of the catheter 100. As a simplified example, if the physician actuates the right most pull wire 105 expecting that this will cause the catheter 100 to deflect to the right, the catheter 100 may move unexpectedly to the left if the catheter 100 is rolled 180 degrees such that the right most pull wire 105 is positioned on the left side of the catheter 100. The physician may estimate the roll position of the catheter 100 based on the roll position of the proximal end of the catheter 100. However, due to the complex shape of the vasculature, the roll position at the proximal end of the catheter 100 may not (and often does not) directly correspond to the roll position at the distal end 103 of the catheter 100. Thus, to understand how actuation of the pull wires 105 will cause the distal portion of the catheter 100 to deflect, one must generally understand the roll position at the distal portion of the catheter 100.

Considering FIG. 2B further, one can see that the roll position of the distal portion of the catheter 100 is not readily discernible. As will be described in more detail below, this application offers new devices, systems, and methods for determining the roll position of the distal end 103 of the catheter 100. Increasing a physician's understanding of the roll position of the distal end 103 of the catheter 100 can greatly facilitate navigation and improve the experience of driving or controlling the catheter 100.

Out-of-Plane or Incline Angle Detection for Endovascular and Other Intraluminal Tools As discussed in the preceding section, in some embodiments, such as the embodiment illustrated in FIG. 2A, a catheter 100 can include a marker 107 (or a plurality of markers) positioned on the distal end 103 thereof. In some embodiments, such as the illustrated embodiments, the marker 107 comprises a ring positioned on the distal end 103. The marker 107 can be radio-opaque such that it can be easily identifiable within a medical image, such as, for example, the medical image shown in FIG. 2B. As described in this section and throughout this application, the shape of the marker(s) 107 within the two-dimensional image can be analyzed to determine the out of the plane angle or incline of the catheter 100. In other words, the two-dimensional projection of the three-dimensional shape of the marker 107 can be analyzed to determine the out of the plane angle of the catheter 100. The term "incline," as referred to herein, can refer to the degree of angulation of the catheter towards or away from the X-ray source (e.g., into or out of the imaging plane), for example, as shown in FIG. 1D. In some examples, a positive degree of angulation indicates that the catheter is angled towards the X-ray emitter, with a maximum incline of +90-degrees. A negative degree of angulation indicates that the catheter is angled away from the X-ray emitter, with a maximum incline of −90-degrees.

Considering the example of FIG. 2A, in the illustrated orientation, the ring-shaped marker 107 presents or appears as a rectangle having a straight edge at the distal most tip within the two-dimensional plane of FIG. 2A. With this orientation, it can be determined that the distal portion of the catheter 100 lies in the plane of the FIG. 2A (e.g., in the illustrated orientation, the catheter 100 is not curving into or out of the plane of FIG. 2A).

Figure 3C:
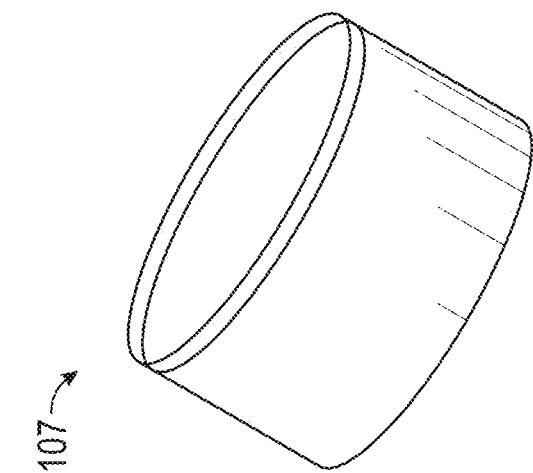
FIGS. 3A-3F illustrate an embodiment of a marker on a distal end of a catheter at different orientations, according to an example.
Figure 3F:
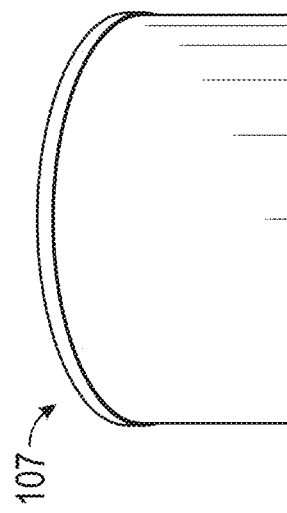
Figure 3B:
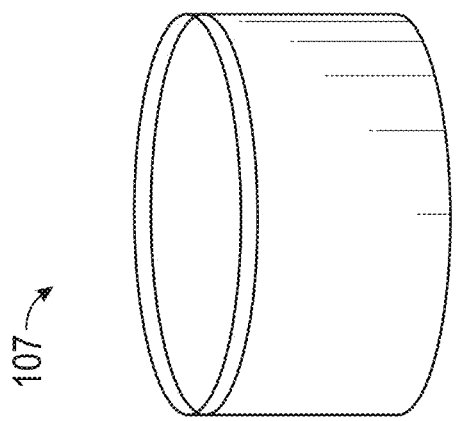
Figure 3E:
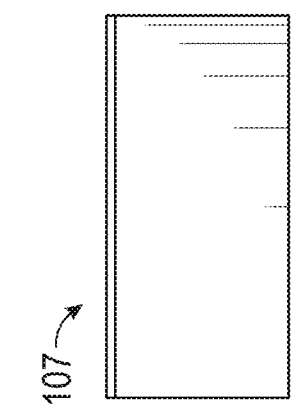
Figure 3A:
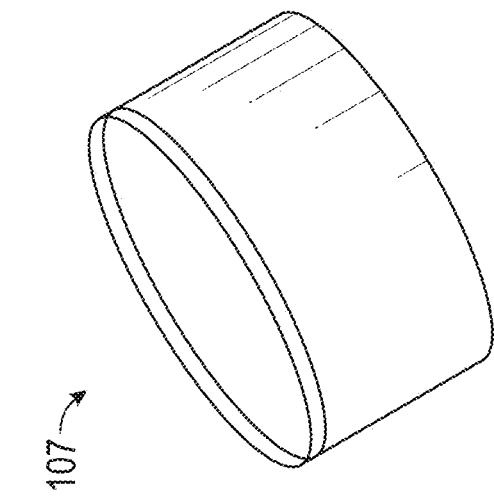

To further illustrate the principles and concepts, FIGS. 3A-3F illustrate the marker 107 in different orientations. In FIGS. 3A-3F, the distal most end of the marker 107 is illustrated with a double line. As before, the marker 107 comprises a ring shape that can be positioned on the end of a catheter, such as the catheter 100 of FIG. 2A. As shown in FIG. 3A, one can see that, within the plane of the FIG. 3A, the marker 107 is generally pointed up and to the left. One can further see that the distal end of the marker 107 presents as an ellipse within the plane of FIG. 3A. Because the entire ellipse is visible, it can be determined that the marker 107 is pointed out of the plane of the page. In contrast, consider FIG. 3F. In FIG. 3F, within the plane of the page, one can see that the marker 107 is pointed straight up. Considering the distal edge of the marker 107, one can only see half of the ellipse (the other half being blocked from view). From this, it can be determined the marker 107 of FIG. 3F is angled into the page.

Figure 3D:
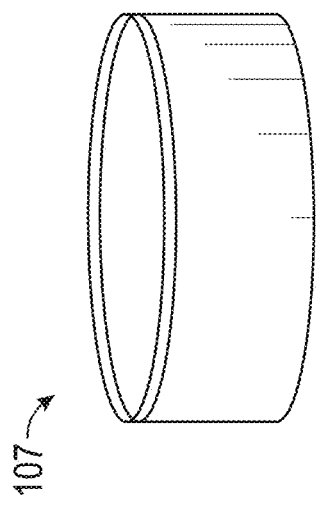

FIG. 3B presents a similar example to FIG. 3F, except, as shown in FIG. 3B, the entire ellipse is visible. From this it can be determined that the marker is angled out of the plane of FIG. 3B. FIG. 3C presents an example where the marker 107 is pointed up and to the right within the plane of FIG. 3C and angled slightly out of the page based on the shape of the ellipse. FIG. 3D illustrates another example where the marker 107 is angled out of the plane of the page. Comparing FIGS. 3B and 3D, one can see that the length of the minor axis of the ellipse is shorter in FIG. 3D as compared to FIG. 3B. This indicates that the degree of the angle out of the page in FIG. 3D is less than the degree of the angle out of the page of FIG. 3B.

If one considers that the marker 107 continues to turn out of the plane of the page, the minor axis of the ellipse will continue to increase in length until the minor and major axes are equal and the distal end of the marker 107 will present as a circle in the plane of the page. FIG. 3E illustrates an example similar to FIG. 2A, in which the marker is pointed upwards, within the plane of the page. At this orientation, the minor axis has decreased to zero, indicating that the marker 107 is pointed upwards within the plane of the page.

From the examples provided, it can be seen that one can analyze the two-dimensional shape created by the ring or circled-shaped marker 107 within a two-dimensional imaging plane to determine the orientation of the marker 107 into and out of the page. Other shapes for marker 107 are possible. For example, the marker 107 need not always comprise a ring shape.

In some embodiments, a computer system, such as or which can include a computer vision system, can be used to (1) detect the shape (e.g., the visible, ellipse, circle, curve, or line) created by the distal end of the ring-shaped marker 107 within the two-dimensional image, and (2) extract or determine the out of the plane angle of the marker 107 or the tool incline from the detected shape. In some embodiments, the computer system may utilize artificial intelligence or machine learning to perform such functionality. In some embodiments, for example, a neural network can be trained to detect the shape created by the distal end of the ring-shaped marker 107 within the two-dimensional image, and extract or determine the out of the plane angle of the marker 107 from the detected shape. In some embodiments, computer vision can be used to define the orientation of the tool along the z-axis.

Figure 4:
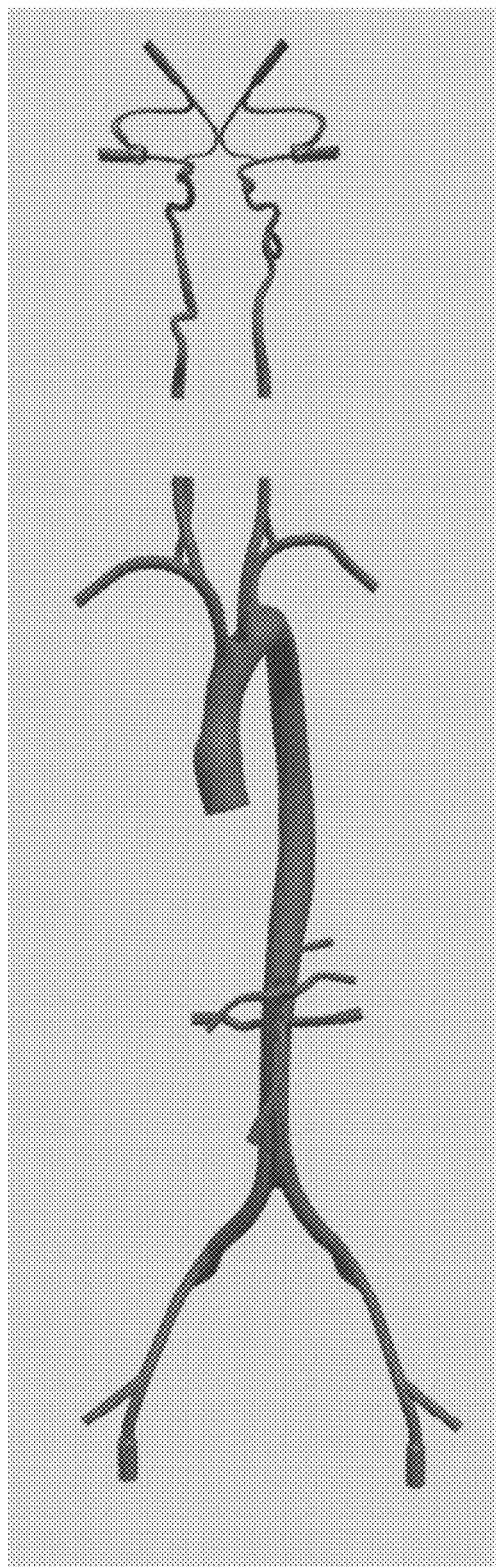
FIG. 4 illustrates an example model of a vascular network of a patient.

As mentioned above, determination of the out of the plane angle of the catheter 100 can be important in improving and/or facilitating navigation through a luminal network, such as the vasculature. In general, the vasculature of a patient will not lie within a single plane. This is apparent considering the model example vasculature provided in FIG. 4. As shown in FIG. 4, for example, the arch of the aorta does move slightly from left to right, but it moves or arches predominately from front to back. Thus, if the patient (on an operating table) is imaged from the top down, a tool navigating through the arch of the aorta will be moving significantly out of the plane of the imaging device. To fully understand this motion, the angle of the catheter 100 out of the page can be determined as described above.

Figure 5A:
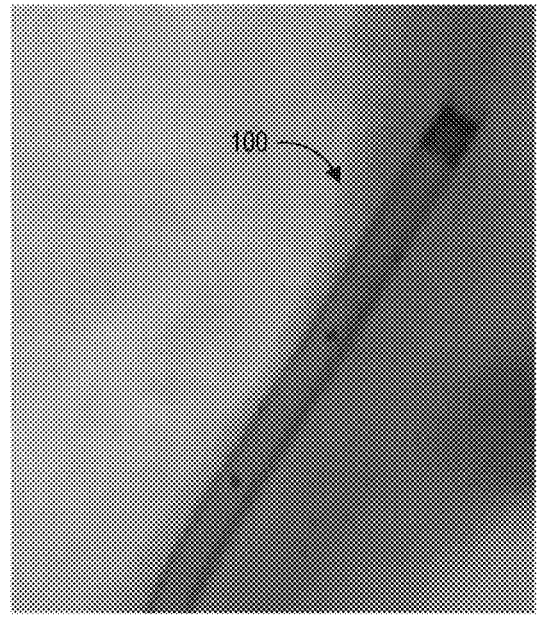
FIG. 5A is an example fluoroscopic image of a catheter navigating through the vasculature.
Figure 5B:
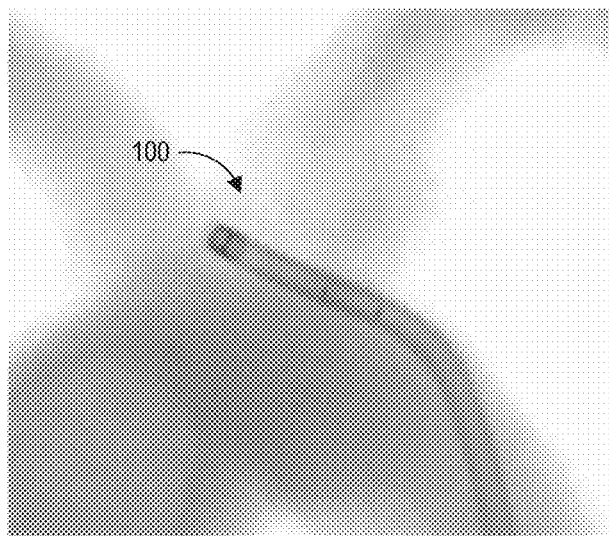
FIG. 5B is another example fluoroscopic image of a catheter navigating through the vasculature.

FIGS. 5A and 5B provide additional example medical images of a catheter, such as the catheter 100 of FIG. 2A, navigating through vasculature. These figures illustrate how the catheter 100 moves at an angle into and out of the plane of the medical image based on the portion of the anatomy through which the catheter 100 passes. For example, as shown in FIG. 5A, which illustrates the catheter 100 navigating through a portion of the carotid artery, the distal end 103 of the catheter 100 lies generally within the plane of the medical image, and thus the distal end 103 of the marker 107 does not form an ellipse. In contrast, FIG. 5B illustrates the catheter 100 navigating through a portion of the aortic arch. As shown, the distal end 103 of the marker 107 does forms an ellipse which indicates that the catheter 100 is moving with at an angle that is moving out of the plane of FIG. 5B.

Figure 6C:
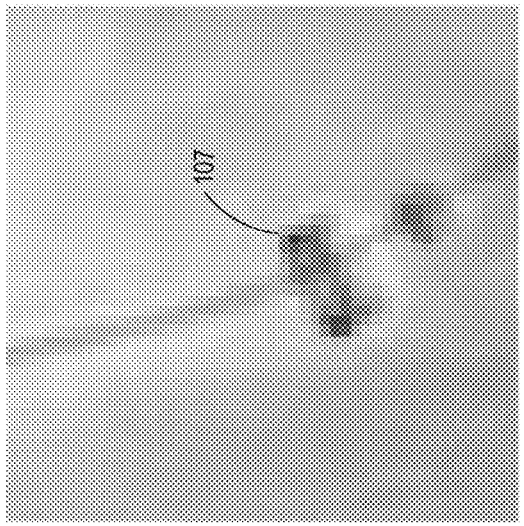
FIGS. 6A-6F illustrate determination of out-of-plane angle based on detection of a shape of the marker within a medical image, according to some examples.
Figure 6F:
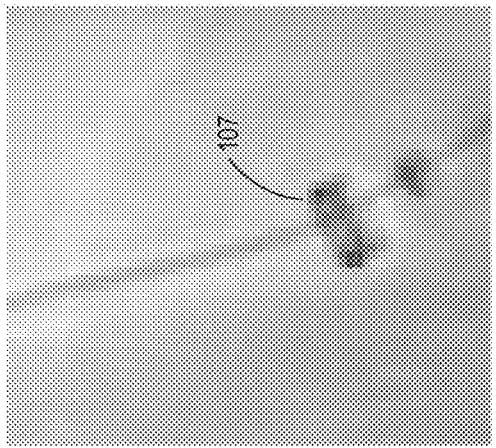
Figure 6B:
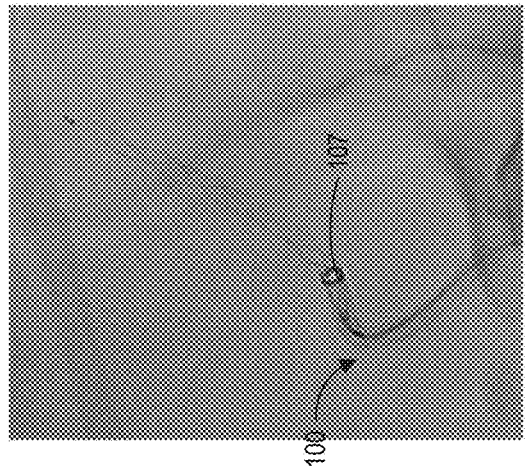
Figure 6E:
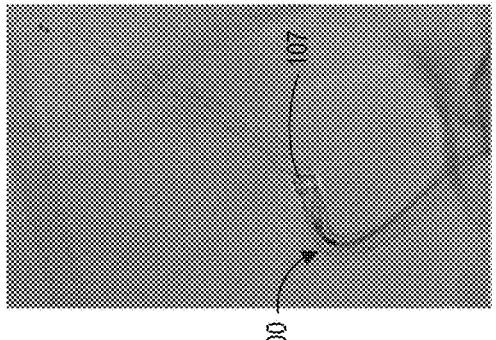
Figure 6A:
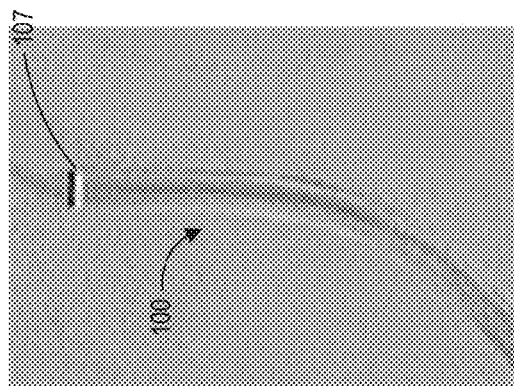
Figure 6D:
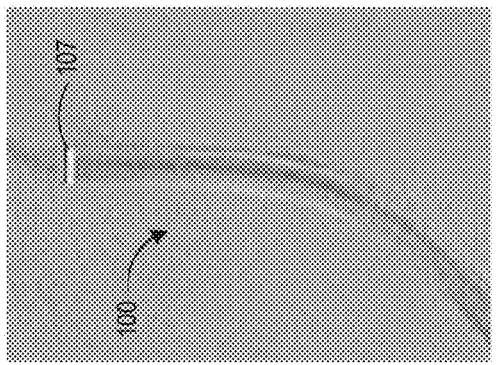

FIGS. 6A-6F provide additional examples of detecting the shape (e.g., the visible, ellipse, circle, curve, or line) created by the distal end of the ring-shaped marker 107 within the two-dimensional image and extracting or determining the out of the plane angle of the marker 107 from the detected shape. FIGS. 6A-6C illustrate three example images, and FIGS. 6D-6F illustrate the same images with the shape of the ring-shaped marker 107 that has been detected and highlighted.

Alternatively or in addition to detecting the shape of the distal tip of the catheter 100 within the plane of the image, other methods or mechanisms may also be employed for determining the out of the plane angle of the catheter 100. For example, in some embodiments, a degree of angulation may be presumed for each vessel through which the catheter 100 passes, for example, based on the general or average angulation of that vessel across the population. In some embodiments, the angulation of a vessel can be determined based on a CT scan. In some embodiments, an additional medical image at a different orientation than the first medical image (e.g., a lateral angiographic view) can be provided. In some embodiments, the medical imager can be moved so as to gain an understanding of the out of the plane angulation.

Although many of the preceding examples have described the use of a ring-shaped marker 107, other types of markers or fiducials can be used as described further below.

Incline Sign Detection for Endovascular and Other Intraluminal Tools

As discussed in the preceding section, the magnitude of the incline of endovascular and other intraluminal tools can, in some embodiments, be determined by analysis of the elliptical shape of the tool mouth (or a marker, such a ring-shaped marker, included thereon). However, the sign of the degree of angulation is not always readily identifiable solely from analysis of the marker 107 because the elliptical shape may look the same when imaged in two dimensions for both positive angulation and negative angulations of the same degree of incline. To determine whether the incline is positive or negative, an additional method may be desired.

FIG. 7A illustrates one method for determining the sign of the incline of catheter 100 where catheter 100 can include a semicircular marker 110 positioned on the distal end 103 thereof. The semicircular marker 110 can be radio-opaque such that it can easily be identifiable within a medical image. In the illustrated example, the semicircular marker 110 extends around one half of the distal end 103 of the catheter 100. In other embodiments, other portions can be used (e.g., ¼, etc.). In some embodiments, additional fiducials, such as helical fiducial 111 may also be used. As described in this section, the position of the marker 110 within the two-dimensional image can be analyzed to determine the sign of the incline of the catheter 100. The sign of the incline of catheter 100 can be determined by whether the semicircular marker 110 appears to be above or below the distal end 103 in the two-dimensional image.

FIGS. 7B-7C illustrate the appearance of the marker 110 on a catheter tip on an X-ray at different inclines. The catheter itself is not shown in these figures. As shown, the semicircular marker 110 in combination with helical fiducial 111 will produce a different appearance in the two-dimensional image when inclined at the same angle, but at different signed inclines (e.g., whether into or out of the plane of the image). For example, the magnitude of the incline could be determined to be 45-degrees using a method such as the ring-shaped marker method described above. The semicircular marker 110 in combination with helical fiducial 111 could then be used to determine the signed incline. For example, in FIG. 7B, the catheter tip is inclined at negative 45-degrees, and in FIG. 7C, the catheter tip is inclined at positive 45-degrees.

In some embodiments, a computer system, such as a computer vision system, can be used to (1) detect the position of the semicircular marker 110 in combination with helical fiducial 111 within the two-dimensional image, and (2) extract or determine the sign of the tool incline from the detected position. In some embodiments, the computer system may utilize artificial intelligence or machine learning to perform such functionality. In some embodiments, for example, a neural network can be trained to detect the position of the semicircular marker 110 in combination with helical fiducial 111 within the two-dimensional image, and extract or determine the sign of the tool incline from the detected position. It should be noted that in some embodiments, the machine learning algorithm does not hardcode the aforementioned approach. Instead, the machine learning algorithm trains a deep neural network to directly predict the incline angle from the input of the X-ray image.

Figure 7D:
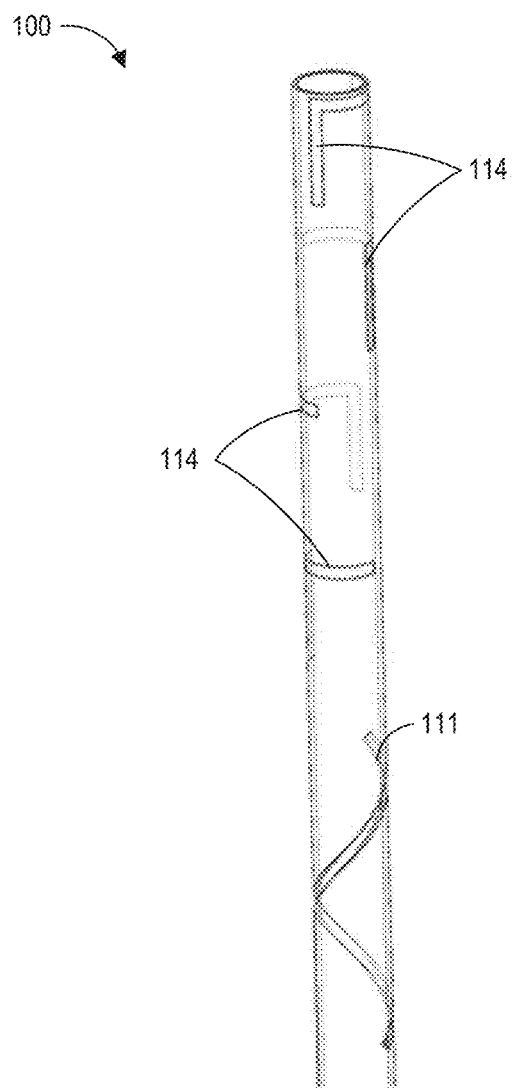
FIG. 7D illustrates an additional example of a catheter including different marker types that can be configured to allow for, among other things, determination of the sign of the incline of the catheter.

FIG. 7D illustrates an additional example of a catheter 100 including a helical marker 111 and additional markers 114. In the illustrated embodiment, the additional markers 114 include a semi-circular portion that extends partially around the radius of the catheter 100 and a tail portion that extends along longitudinally along the catheter.

Figure 8A:
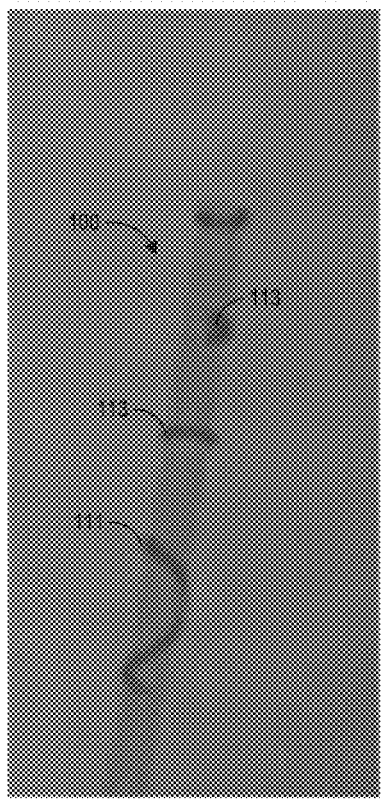
FIGS. 8A-8B illustrate example fluoroscopic images of a catheter including an example of a non-circumferential ring configured to allow for determination of, among other things, both the sign and magnitude of the incline of the catheter.
Figure 8B:
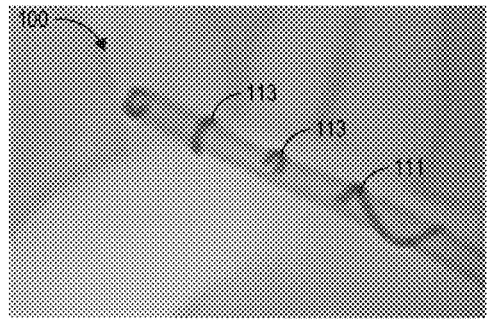

FIGS. 8A-8B illustrate provide an additional example of determination of the sign and magnitude of incline of catheter 100, where the catheter 100 can include one or more non-circumferential rings 113. In the illustrated embodiment, the non-circumferential rings are semi-circular, extending part way around the catheter 100. In some embodiments, the non-circumferential rings 113 can be radio-opaque such that it can easily be identifiable within a medical image. The appearance of the non-circumferential rings 113 can be analyzed to determine the sign and magnitude of the incline of the catheter 100. The sign and magnitude of the incline of catheter 100 can be determined by the unique appearance of the non-circumferential rings 113 in the two-dimensional image at varying degrees of incline, both positive and negative. In some embodiments, non-circumferential rings 113 are arranged in an asymmetrical design. That is, in some embodiments, the non-circumferential rings 113 are each positioned at a different rotational position around the catheter 100. In the illustrated embodiments, the non-circumferential rings are positioned at 90 degree offsets. In some embodiments, non-circumferential rings 113 are multiple ellipses offset from each other.

Figure 8C:
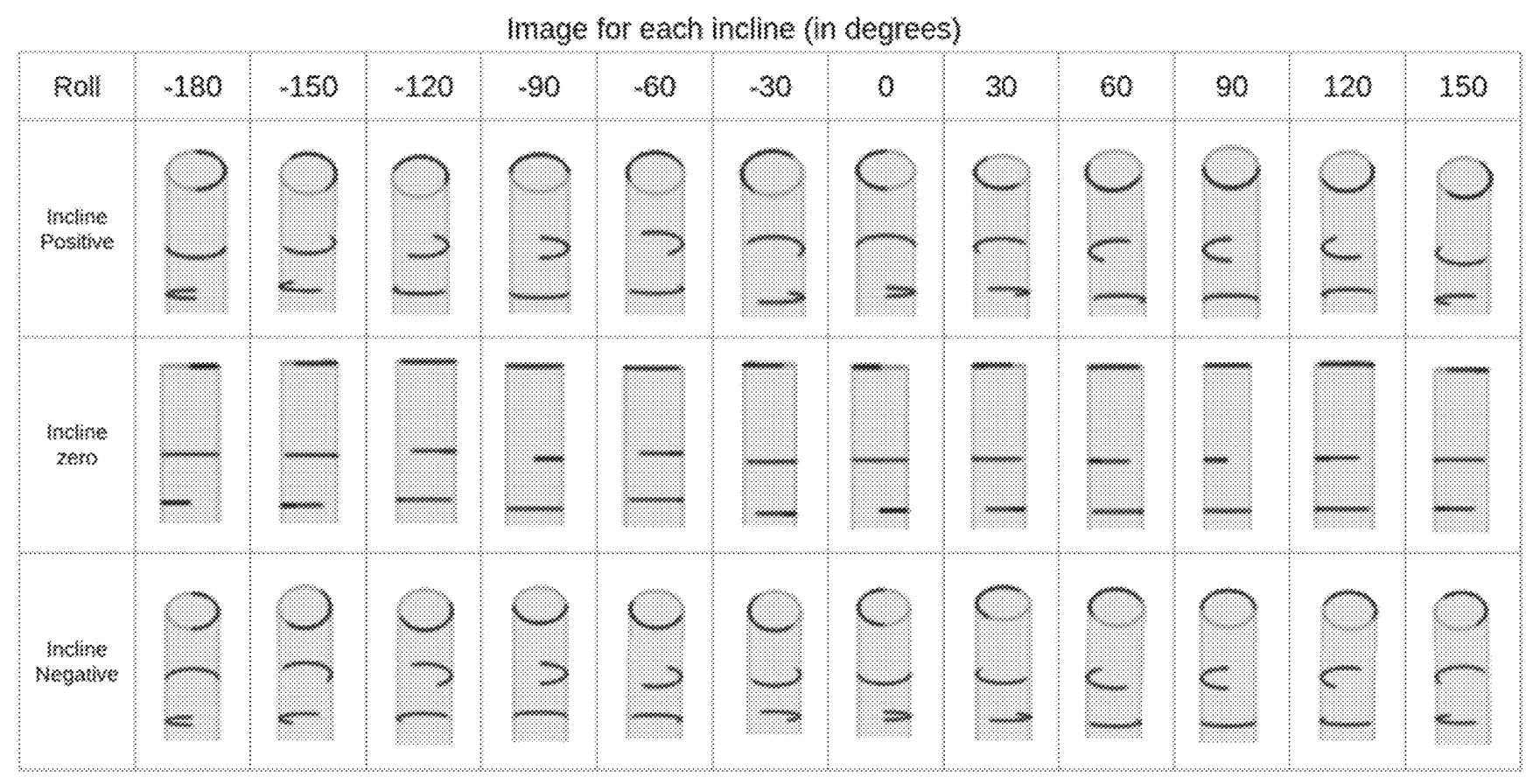

FIG. 8C illustrates how an example arrangement of non-circumferential rings 113 positioned on a distal end of a catheter may provide a unique appearance at different inclination and roll angles. Images are provided at positive, neutral (i.e., zero), and negative inclinations, as well as at different roll positions provided in 30 degree increments. As shown, each of the 36 different illustrated positions provides a unique appearance. By detected, for example, using computer vision, this appearance within a medical image, the incline (including its sign) and the roll of the catheter can be determined. While FIG. 8C illustrates how the radio-opaque markers provide different two-dimensional appearances for different roll positions at 30 degree increments and for different positive, neutral (zero), and negative inclines, the illustrated increments are not intended to be limiting.

In some embodiments, the radio-opaque markers provide unique or visually distinguishable two-dimensional appearances at all different roll or incline positions. In some embodiments, the radio-opaque markers provide unique or visually distinguishable two-dimensional appearances at different roll or incline positions within increments of about, at least, or at most 1 degree, 2 degrees, 3 degrees, 4 degrees, 5 degrees, 7.5 degrees, 10 degrees, 12.5 degrees, 15 degrees, 17.5 degrees, 20 degrees, 25 degrees, 30 degrees, or 40 degrees. That is, in some embodiments, the radio-opaque markers are configured with a three-dimensional shape that, when viewed within the two-dimensional plane of a two-dimensional medical imaging device, provides a unique or visually distinguishable appearance that can be distinguished at the different incremental roll or incline angles listed above. The above listed increments can be considered minimum resolutions for the system or the minimum change in roll or incline that is detectable by the system.

Tool Position and Heading for Endovascular and Other Intraluminal Tools

Figure 9A:
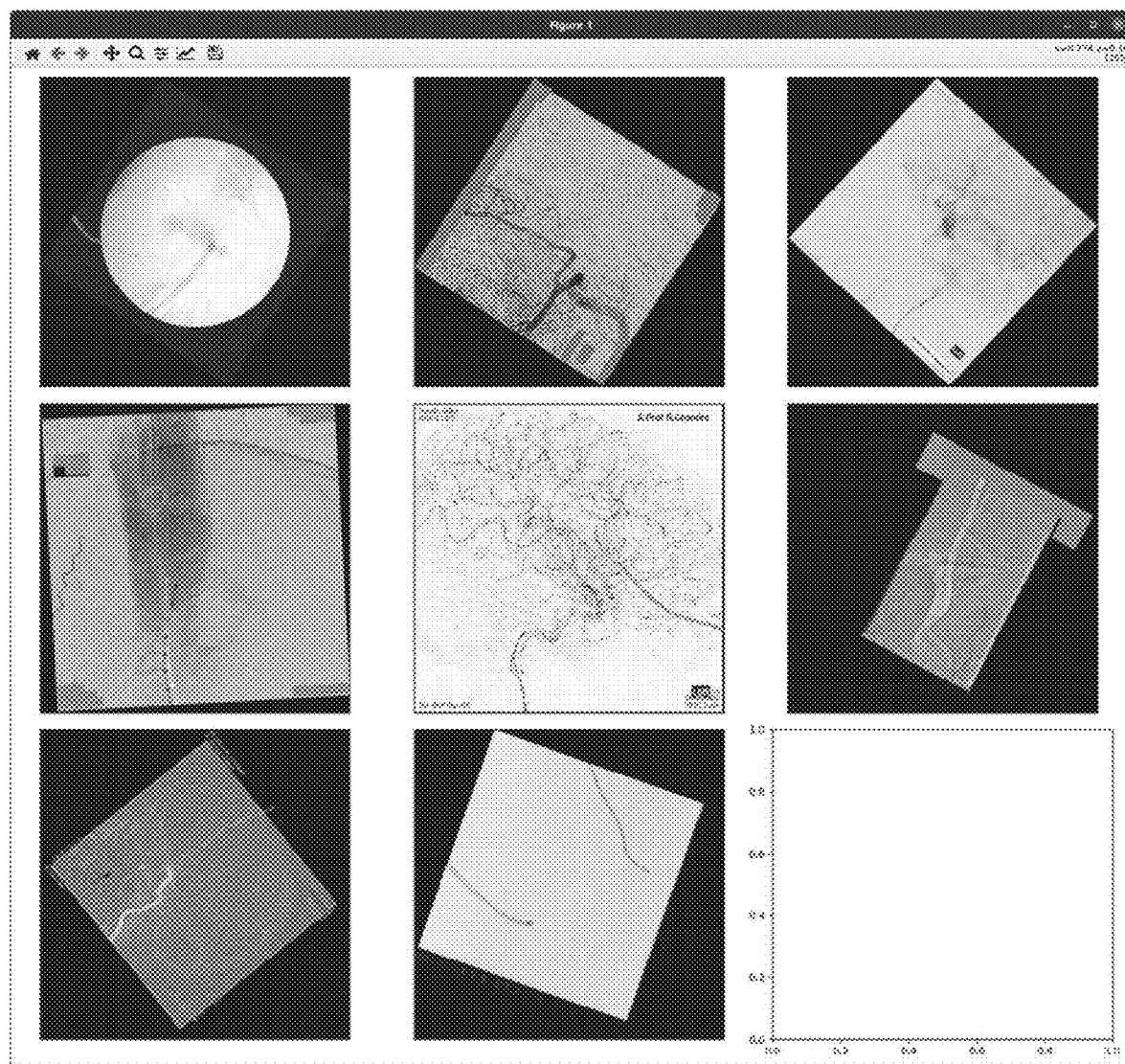
FIG. 9A illustrates examples of projections of three-dimensional generated catheters onto real world two-dimensional X-ray images, according to some examples.
Figure 9C:
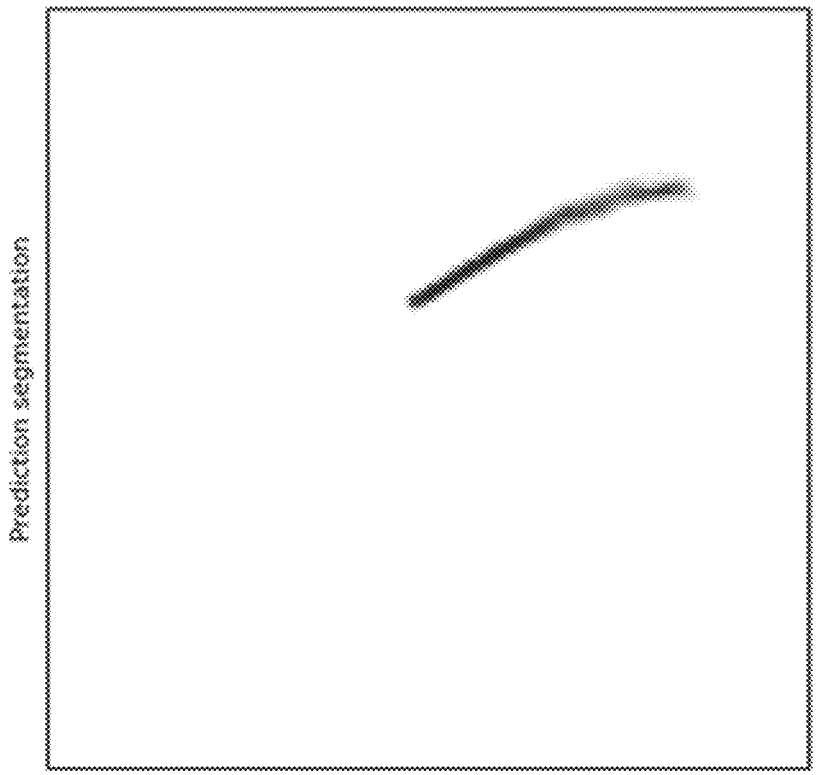
FIGS. 9B-9C illustrate an example prediction of a trained deep neural network for predicting a position of a body of a catheter body, according to an example.
Figure 9B:
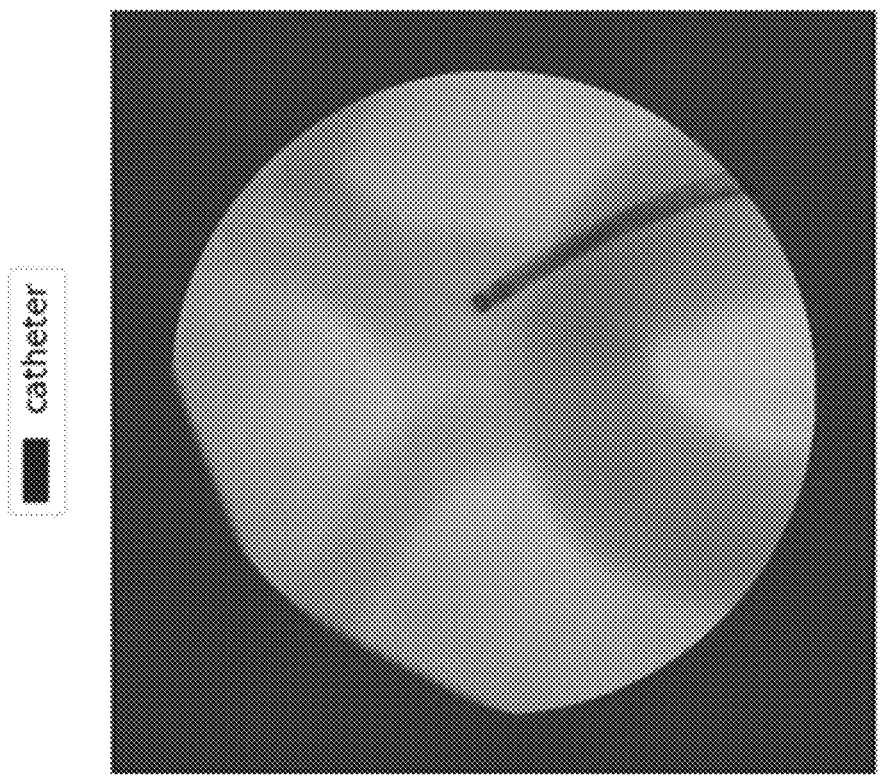

FIG. 9A illustrates examples of projections of three-dimensional generated catheters onto real world two-dimensional X-ray images. FIGS. 9B-9C illustrate an example prediction of the trained deep neural network for predicting where the catheter body is. As noted above, position can refer to translation of endovascular and/or other intraluminal tools along the x, y, and z directions. In some embodiments, instead of determining the three-dimensional position of the instrument (z, y, and z), only the two-dimensional (x and y) position is used. This can be because estimating the z position (i.e., depth) may require calibrating the X-ray camera to obtain determine intrinsic parameters thereof. While this is feasible, it would likely (1) add a burdensome pre-operative image calibration step, (2) may not help that much because motion planning is primarily done in two-dimensions, and (3) we the C-arm can be rotated to obtain a Z position estimate.

In some embodiments, the system may be configured to predict where the full tool body is, and then from this tool body we the two-dimensional tip location can be extracted. This approach may be beneficial because the tool body provides a very strong training signal for learning deep neural network segmentation models. That is, in some instances, it may be easier for a neural network of computer vision algorithm to detect the body of a catheter and then extract the location of the tip from there. In some embodiments, catheter kinematics are further used refine this estimate.

Figure 9D:
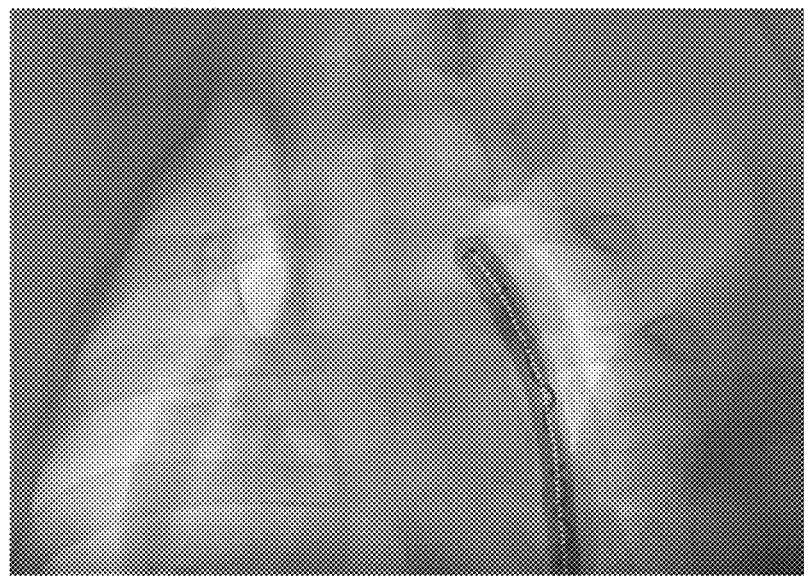
FIG. 9D illustrates an example determination of a centerline of a catheter.
Figure 9E:
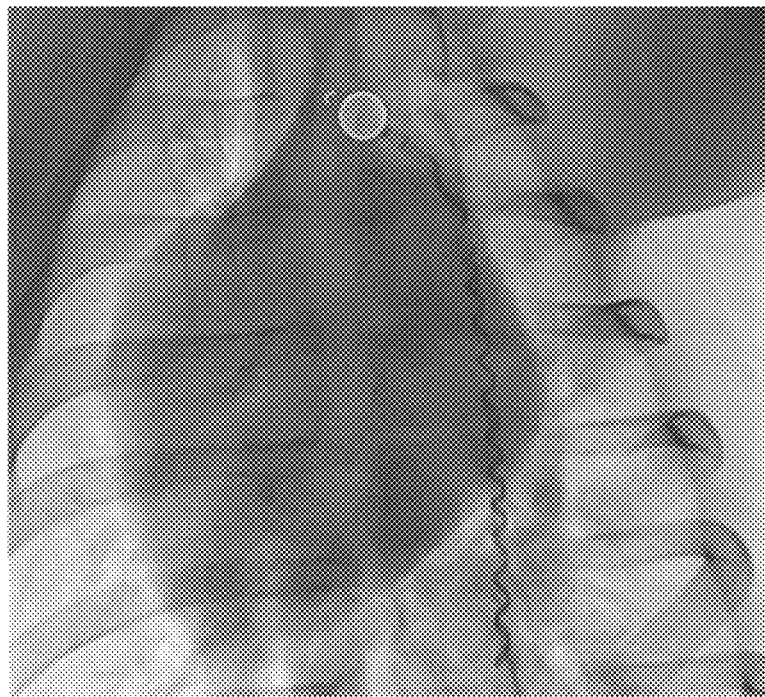
FIG. 9E illustrates an example determination of a position and heading of a catheter.

For example, a deep neural network can be used to estimate the two-dimensional centerline position of the catheter based on one or more images of the catheter navigating within the body. FIG. 9D illustrates an example, in which the neural network has identified the catheter within the image, superimposed its estimated centerline onto the image, and highlighted the catheter. Once the centerline of the catheter has been identified within the image, the two-dimensional position can be directly extracted by computing the most distal position along the centerline. Similarly, the heading of the catheter can also be directly extracted from the body estimate by computing the vector of the tip of the body line. FIG. 9E illustrates an example in which the distal tip position and heading angle have been determined and the image has been updated to include a highlight identifying the position and an arrow indicating the heading.

In some embodiments, a machine learning algorithm for estimating the position of a catheter and/or other tool may use the following approach. First, the image generation procedure is modified by drawing the catheter on top of tangible X-ray images (e.g., as shown in FIG. 9B). This process may have the advantage of training the deep neural network with realistic noise and occlusions that would be seen in actual X-rays, making the system robust to real world conditions.

Second, the two-dimensional x and y position is estimated. In some embodiments, radio-opaque markings may be added to the tool body, such as, for example, a full-length helix, to assist with the identification. In some embodiments, the three-dimensional x, y, and z position may be estimated instead. However, estimation of the Z position may require calibration of the X-ray camera to obtain its camera intrinsic, which requires an additional step of a pre-operation image calibration. In some instances, the two-dimensional position estimation will be preferable so the pre-operation image calibration step does not need to be completed and because the z position may not be necessary because motion planning is primarily conducted in two-dimensions. Further, a z position estimate can be obtained by rotating the C-arm. Using this method, the two-dimensional x and y position of the full tool body may be predicted. Thereafter, the two-dimensional x and y position location of the tool tip (such as, for example, the distal end 103 of catheter 100) can be determined. This approach may be used because the tool body provides a very strong training signal for learning deep neural network segmentation models. In some embodiments, catheter kinematics may be used to further refine the position estimate.

As noted above, heading can refer to a measure of angulation or articulation about the z-axis and/or where the device is pointing in the image plane. To determine the heading of endovascular and/or other intraluminal tools, such as a catheter, the deep neural network prediction of the catheter body position may be used. Based on the prediction of the two-dimensional x and y position of the catheter tip, a second position located on the catheter body may be determined. The second position may be an infinitesimal distance from the tool tip in a direction along the catheter body. The heading angle of the catheter may then be calculated using trigonometry based on the x and y position of the tool tip and the second position along the catheter body.

Roll Angle Detection for Endovascular and Other Intraluminal Tools

As noted above, radio-opaque markers can be placed at the distal tip 103 of a catheter 100 to improve the visibility of the catheter 100 in a medical image (see FIGS. 2A and 2B). In some embodiments, these markers are symmetric about the tools axis and thus do not provide any information related to the roll angle of the catheter. As described in this section, the degree of rotation of a tool about its centerline may be informed by the addition of radio-opaque rotation fiducials. Numerous configurations of radio-opaque rotation fiducials can be utilized to determine the degree of tool rotation, provided the configurations result in a unique X-ray appearance of the tool at differing degrees of rotation. While multiple configurations will be disclosed with reference to certain embodiments, it will be understood that various changes may be made, and equivalents may be substituted for elements thereof without departing from the scope of the disclosure. For example, markers 108 that are rotationally asymmetric can be utilized on the catheter 100 and configured to provide information from which the roll angle of the catheter 100 can be determined. In some embodiments, a computer vision algorithm can be used to detect and analyze the positions of the markers 108 to determine the rotation or roll of the catheter 100 about its longitudinal axis. As described above, the rotation of the catheter 100 determines how an actuation of a given pull wire will move the catheter 100. Thus, an accurate understanding of the roll angle of the catheter 100 can be important for successful navigation of the catheter 100 through the vasculature.

FIGS. 11A and 11B illustrate side and top views respectively of a distal portion of a catheter 100 that has been configured with markers 108 from which the roll angle of the catheter 100 can be determined. In this embodiment, the catheter 100 includes markers 108A-108D configured as radio-opaque fiducials (e.g., dots) placed at different distances from the distal tip 103, at differing angles/arcs from the center of the tool. This configuration allows the catheter 100 to take on a unique appearance depending on its rotation around its longitudinal axis. In some embodiments, the markers may be other radio-opaque fiducials, such as, for example squares, circles, diamonds, and/or the like.

In the illustrated embodiment, a first marker 108A is positioned a first distance 2D (twice the diameter of the tool) from the distal tip 103 and at a 45-degree rotational offset with respect to a first pull wire 105. A second marker 108B is positioned an additional distance 2D from the distal tip 103 (4D) and at a 135-degree rotational offset with respect to the first pull wire 105. A third marker 108C is positioned an additional distance 2D from the distal tip 103 (6D) and at a 225-degree rotational offset with respect to the first pull wire 105. A fourth marker 108D is positioned an additional distance 2D from the distal tip 103 (8D) and at a 315-degree rotational offset with respect to the first pull wire 105. In some embodiments, the rotational offset of first marker 108A from the first pull wire may be, for example, 0-degrees, 5-degrees, 10-degrees, 15-degrees, 20-degrees, 25-degrees, 30-degrees, 35-degrees, 40-degrees, 45-degrees, 50-degrees, 55-degrees, 60-degrees, 65-degrees, 70-degrees, 75-degrees, 80-degrees, 85-degrees, 90-degrees, and/or the like, with the second marker 108B, third marker 108C, and fourth marker 108D being an additional 90-degrees, 180 degrees, and 270-degrees respectively rotationally offset from first marker 108A. In some embodiments, the distance 2D is approximately 5 mm.

In the illustrated example, each marker 108 is positioned at a longitudinal distance that is twice the diameter D of the catheter 100 below the marker 108 above it (or below the distal tip 103 for the first marker). This need not be the case in all embodiments, and other spacings are possible. In the illustrated example, each marker 108 is positioned at 90-degree offsets and between the adjacent pull wires 105. Again, this need not be the case in all embodiments and other spacings are possible. Further, in FIG. 6A, the catheter 100 is illustrated as transparent, allowing all four markers 108 to be visible. It should be appreciated, however, that in the illustrated example, markers 108A and 108D are on the back side of the catheter 100 (the side facing away relative to the orientation of the image) and thus would not be visible if the catheter were not illustrated as transparent.

With such a configuration or other suitable configurations, the appearance of the markers 108A-108D within a medical image provides a unique appearance from which the roll of the catheter 100 can be determined. FIGS. 12A-12D provide various examples of the catheter 100 at different orientations. In each of FIGS. 12A-12D, both a model of the catheter and a corresponding image of the catheter are shown. FIGS. 12A-12D illustrate that for each roll position, the appearance of the markers 108A-108D is different, thus allowing for roll determination.

In some embodiments, determining roll from the markers 108A-108D can be accomplished as follows: (1) the locations of the markers 108A-108D within an image can be determined, in some embodiments, this is accomplished through computer vision or a neural network that has been trained to identify the markers 108A-108D; (2) the centerline of the catheter 100 can be determined using, for example, computer vision or a neural network; (3) the distance (with appropriate sign, positive or negative) between each of the markers 108A-108D and the centerline can be determined; (4) the signed distance between the markers and the centerline can be used to determine the roll angle using geometry principles.

Use of four markers 108A-108D, for example, as shown in FIGS. 11A-11B and FIGS. 12A-12D, can be advantageous for various reasons. For example, because each marker 108A-108D is placed at a different distance from the distal tip 103, they can each be uniquely identified by that distance. This can allow the machine learning model and/or loss to be much more robust and/or generalizable. Use of four markers 108A-108D may also prevent against or eliminate angle aliasing, for example, allowing for full determination of roll between 0 and 360 degrees. Because the markers 108A-108D are equidistantly spaced along the longitudinal axis, the markers 108A-108D can be analyzed to determine out-of-of plane rotations. Further, use of four markers 108A-108D can allow for determination of the centerline of the catheter 100. Use of markers 108A-108D and four pull wires 105 can also facilitate control and verification.

In some embodiments, increasing the axial distance between the markers 108A-108D, can increase the signal to noise ratio, for example, allowing the markers 108A-108D to be more easily identified within the medical image. In some embodiments, more than four markers may be used to determine the roll of the catheter 100. In some embodiments, less than four markers may be used to determine the roll of the catheter 100.

Figure 13A:
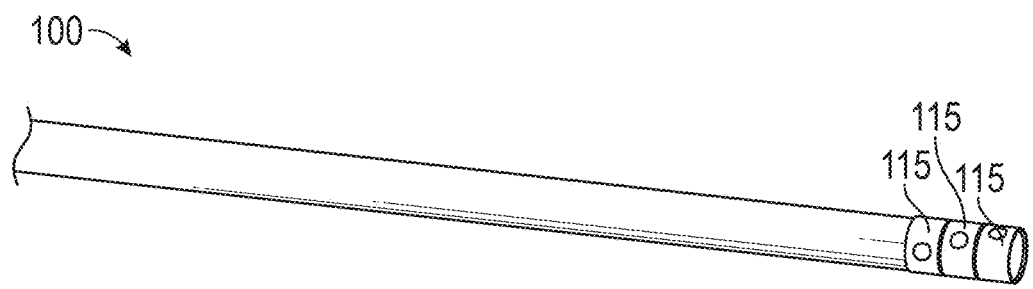
FIGS. 13A and 13B are perspective and side views of another embodiment of a catheter that includes markers configured to allow for determination of a catheter roll angle.
Figure 13B:
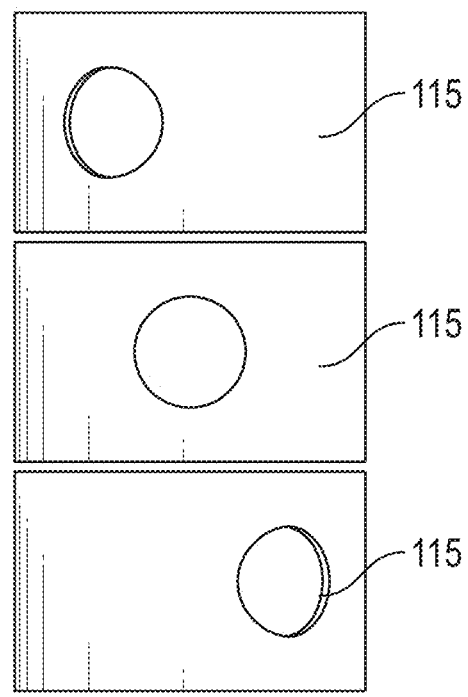

FIGS. 13A and 13B illustrate another embodiment of markers 115 that can be used to determine roll angle of a catheter 100. FIG. 13A is a perspective view of a distal end of a catheter 100 including markers thereon. FIG. 13B is a side view of the markers 115. In the illustrated embodiment of FIGS. 13A and 13B, multiple ring-shaped markers 115 are included. Each ring-shaped marker 115 can include a through hole formed therethrough. When the ring 115 is rotated such that the holes align, there will be a visible gap in the ring. When the ring 115 is rotated such that the holes do not align, the ring will appear solid. This distinction may be detectable through a centroid detection algorithm or a computer vision algorithm trained for this type of device. In other embodiments, the hole need not be circular, the hole may be, for example, any polygonal shape.

As shown in FIGS. 13A and 13B, multiple rings 115 may be stacked at set rotations, such that the rotation of the tool can be determined by identifying which of the rings 115 presents a visible gap.

In some embodiments, radio-opaque sleeves or other features can be coupled to the pull wires. In such cases, a computer vision algorithm can be configured to either detect the features at opposite sides of the catheter or to detect when the features overlap. In either case, these features would allow the computer vision system to assess if the tool is oriented with each pull wire in plane.

Figure 14A:
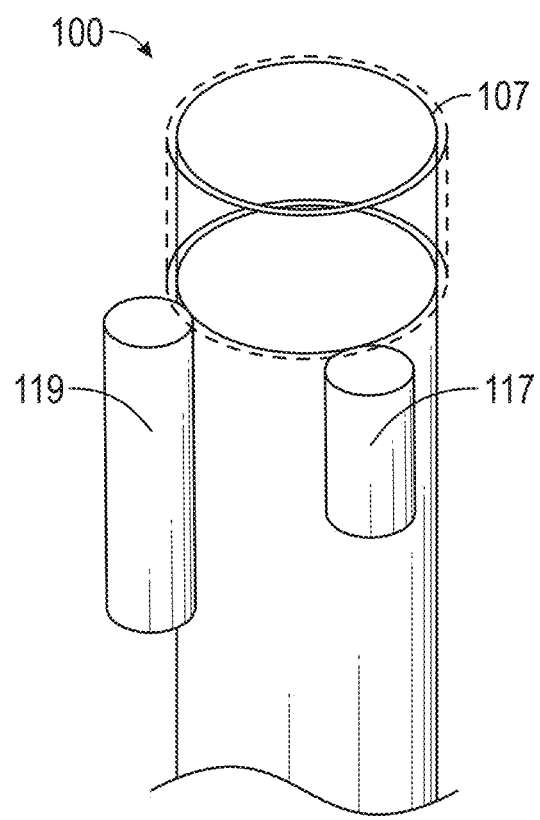
FIGS. 14A and 14B are perspective and top views of another embodiment of a catheter that includes markers configured to allow for determination of a catheter roll angle.
Figure 14B:
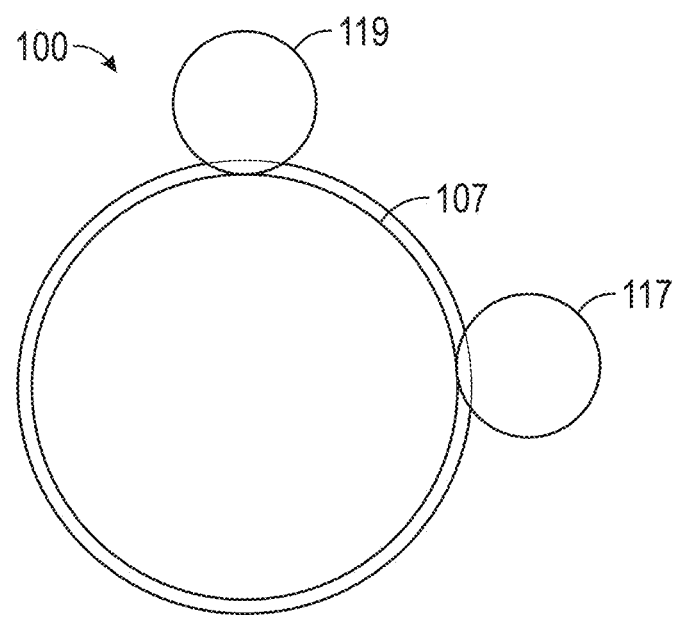
Figure 15A:
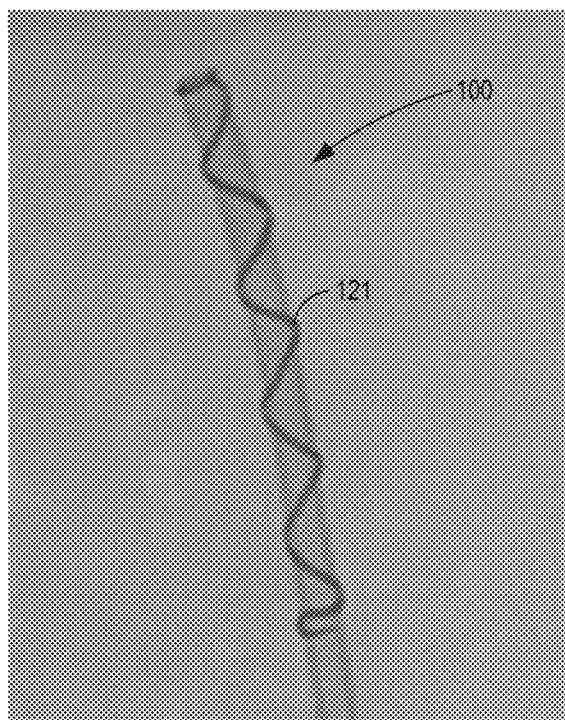
FIGS. 15A-15H illustrate determination of roll angle based on detection of a phase of a sinusoid of a helical fiducial within a medical image, according to some examples.
Figure 15B:
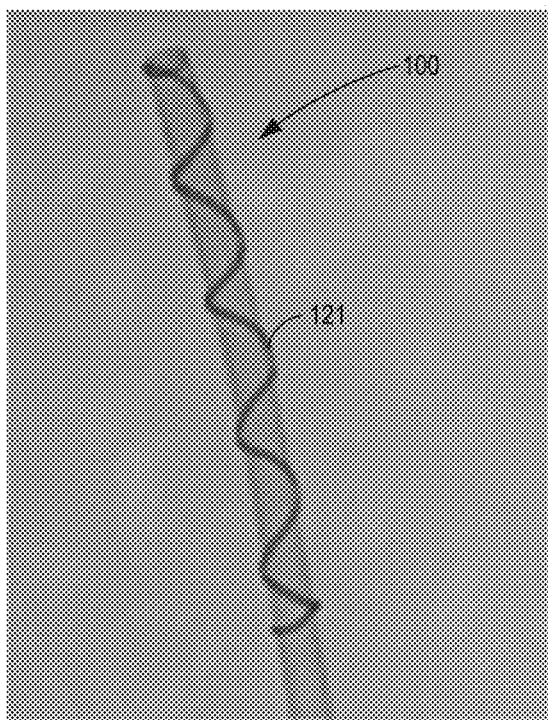
Figure 15C:
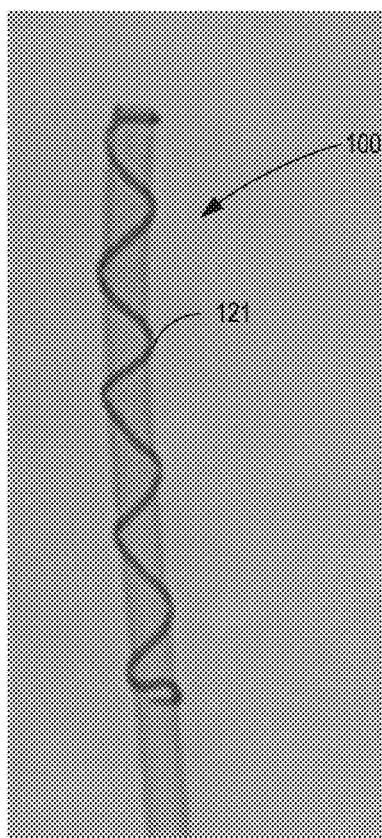
Figure 15D:
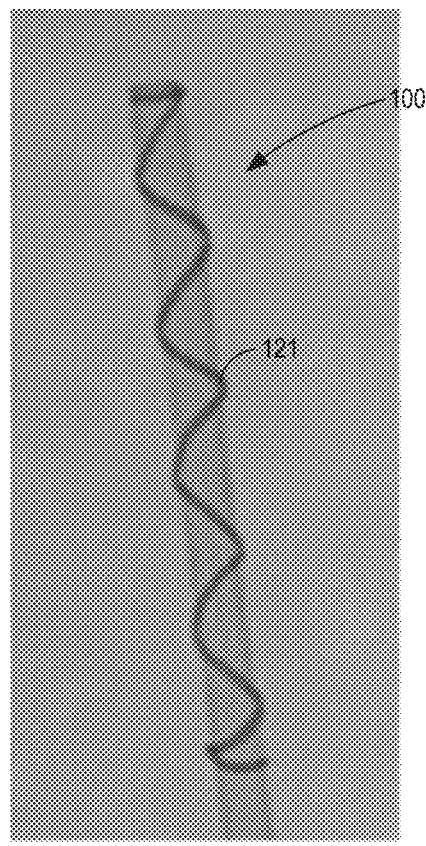
Figure 15E:
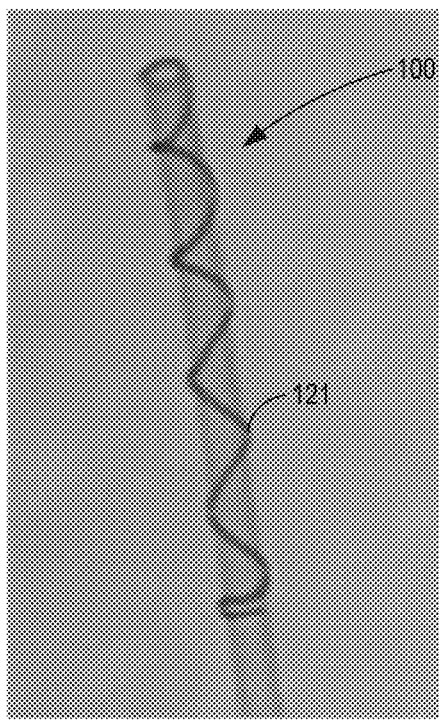
Figure 15F:
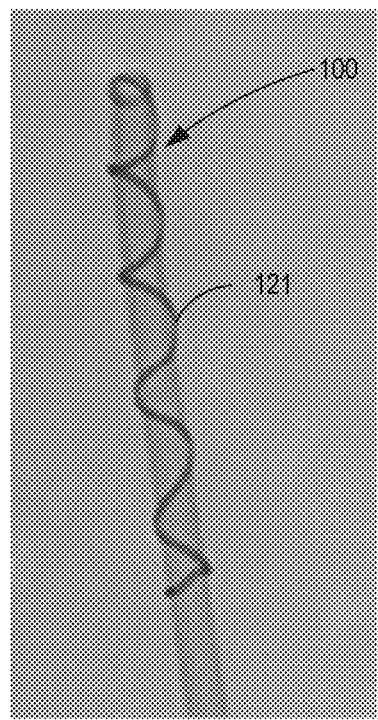
Figure 15G:
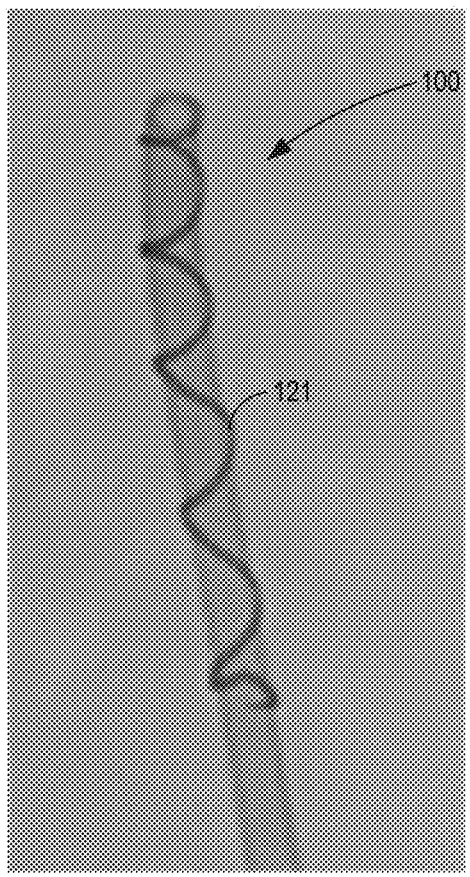
Figure 15H:
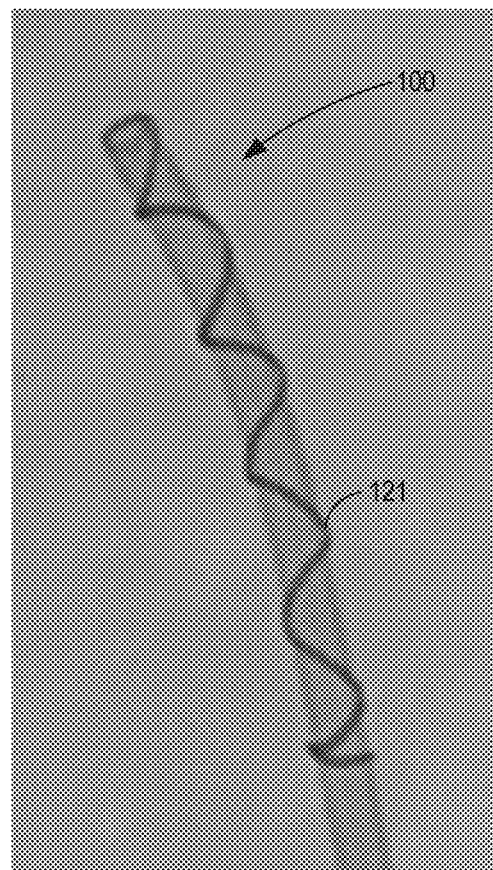

FIGS. 14A and 14B illustrate another embodiment of catheter 100 that includes the use of two markers 117 and 119 of different lengths oriented at 90 degrees with respect to each other. Because the markers 117 and 119 are of different length, the relative position of the markers 117 to marker 119 can be determined, allowing roll angle to be reliably computed using only two markers.

FIGS. 15A-15H illustrate another embodiment of a configuration that may be used to determine the roll of the catheter 100. In this embodiment, a radio-opaque helix fiducial 121 is coupled to catheter 100. In some embodiments, the radio-opaque helix fiducial 121 is approximately sinusoidal such that the phase of the sinusoid can be used to determine the degree of roll. In some embodiments, the phase of the sinusoid may be determined by the location of the radio-opaque helix fiducial 121 closest to the distal end of the catheter 100 and by the location of the radio-opaque helix fiducial 121 furthest from the distal end of the catheter 100, near the base of the cylindrical band. It should be noted that in some embodiments, the machine learning algorithm does not hardcode the phase determination. Instead, the machine learning algorithm trains a deep neural network to directly predict the roll angle form the input X-ray image. FIGS. 15A-15H illustrate X-ray images of catheter 100 at different degrees of roll and different degrees of incline.

Figure 16A:
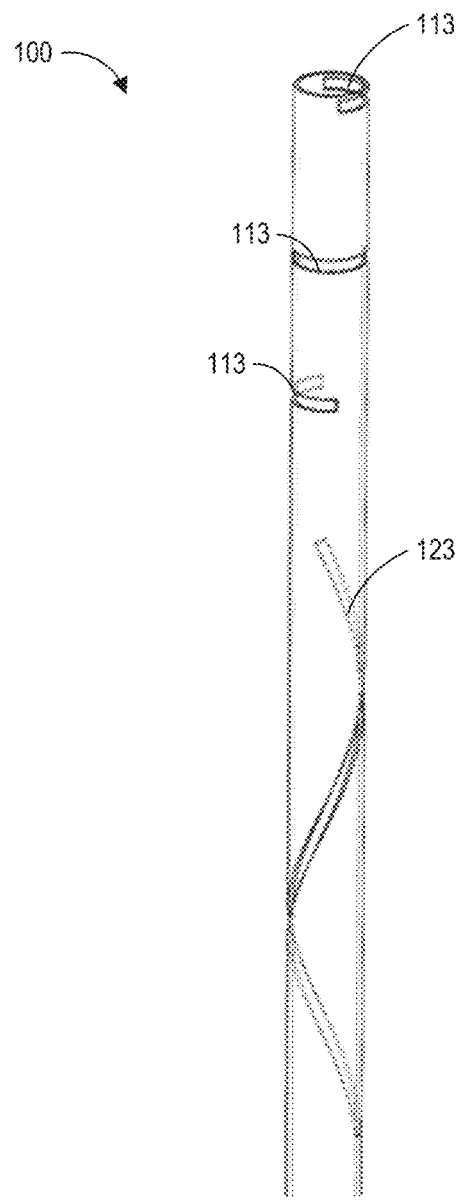
FIG. 16A is a perspective view of another embodiment of a catheter that includes a radio-opaque one and one quarter roll helix fiducial configured to allow for determination of a catheter roll angle.
Figure 16B:
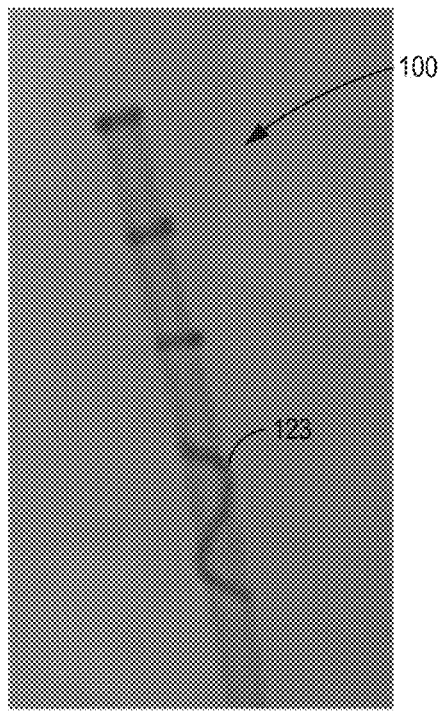
FIGS. 16B-16E show fluoroscopic images of a catheter for determination of a catheter roll angle, according to some examples.
Figure 16C:
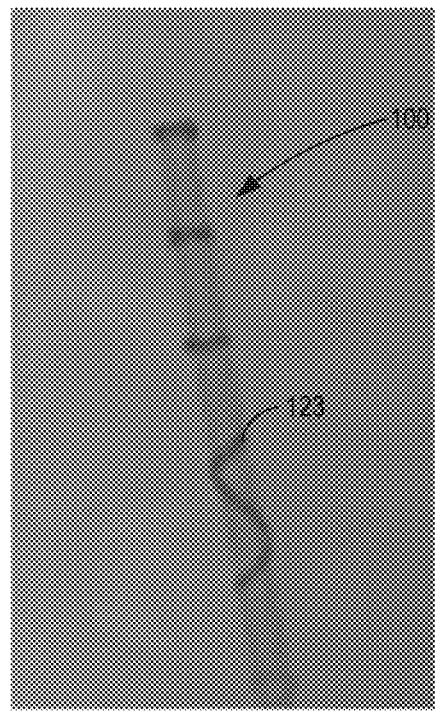
Figure 16D:
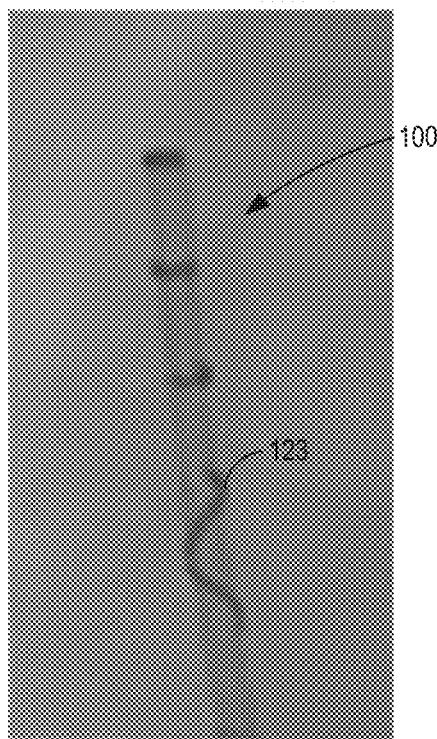
Figure 16E:
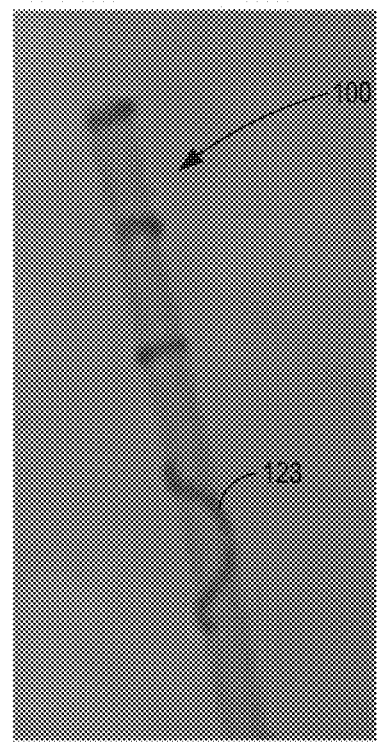

FIG. 16A illustrates another embodiment of a configuration that may be used to determine the roll of the catheter 100. In this embodiment, a radio-opaque one and one quarter roll helix fiducial 123 is coupled to catheter 100, where the helix is made slightly longer than one complete revolution, such that the roll helix fiducial 123 is approximately 1.25 times the articulation length. The degree of roll of catheter 100 can be determined because the roll helix 123 takes on a different appearance depending on the degree of roll. In FIG. 16A, the roll helix fiducial can comprise other lengths greater than or less than one and one quarters. For example, as shown in FIGS. 16B-16E, at different degrees of roll, the roll helix 123 takes on a distinct appearance. In some embodiments, the articulation length is approximately two centimeters. Notably, the embodiments illustrated in FIGS. 16A-16E also include examples of the non-circumferential markers discussed above.

Figure 16F:
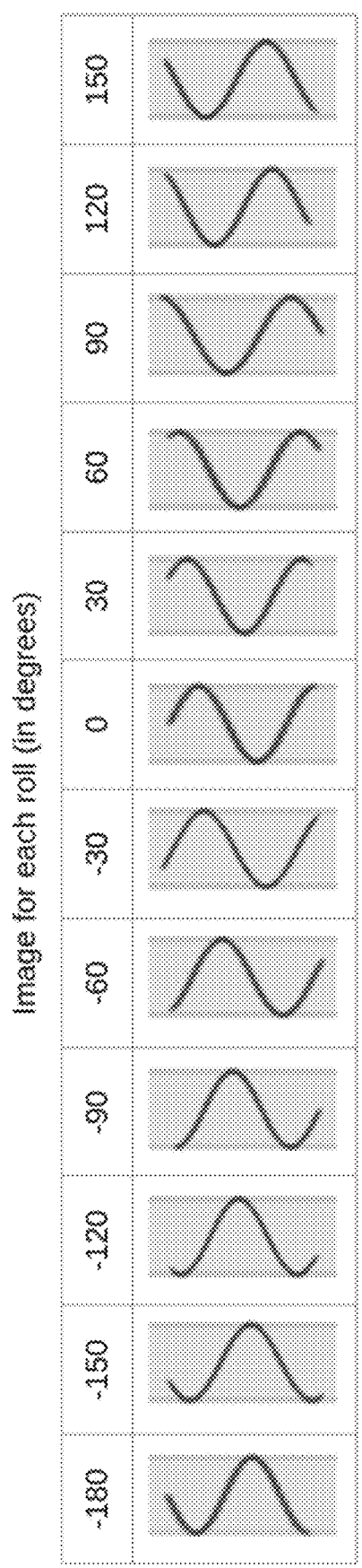
FIG. 16F illustrates the two-dimensional appearance of a radio-opaque marker at different roll positions.

FIG. 16F illustrates the two-dimensional appearance (e.g., as within the plane of medial image) of the helical fiducial 123 of FIG. 16A and different roll positions in 30 degree increments. As shown, each roll position provides a unique appearance which can be used to determine roll, for example, by a computer vision, neural network, or machine learning system. While FIG. 16F illustrates how the radio-opaque markers provide different two-dimensional appearances for different roll positions at 30 degree increments, the illustrated increments are not intended to be limiting.

In some embodiments, the radio-opaque markers provide unique or visually distinguishable two-dimensional appearances at all different roll positions. In some embodiments, the radio-opaque markers provide unique or visually distinguishable two-dimensional appearances at different roll positions within increments of about, at least, or at most 1 degree, 2 degrees, 3 degrees, 4 degrees, 5 degrees, 7.5 degrees, 10 degrees, 12.5 degrees, 15 degrees, 17.5 degrees, 20 degrees, 25 degrees, 30 degrees, or 40 degrees. The above listed increments can be considered minimum resolutions for the system or the minimum change in roll that is detectable by the system.

In some embodiments, the roll angle determined based on the markers of any of these embodiments can be used by a motion planning algorithm to determine how it will move the catheter. In one embodiment, the algorithm can be configured to rotate the catheter until the radio-opaque identifiers aligns with the imaging plane. In another embodiment, the algorithm can measure the rotation of the tool using the radio-opaque identifiers and update which pull wires it uses to execute a maneuver.

Additional Detail

Figure 17A:
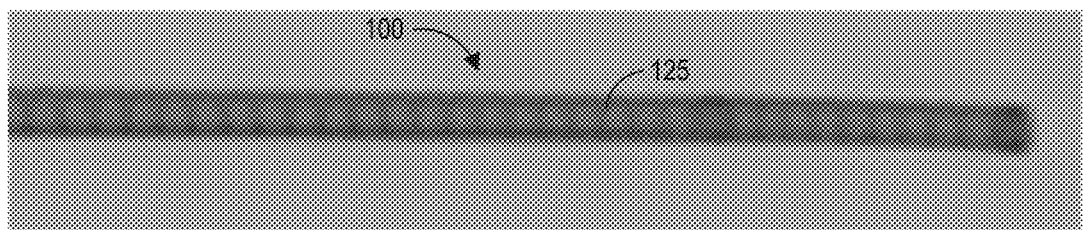
FIGS. 17A-17B illustrate an embodiment of a catheter that includes radio opaque braids can be used to determine roll, according to some examples.
Figure 17B:
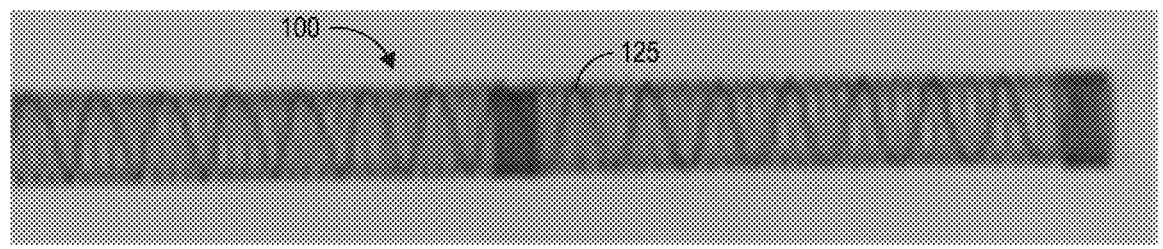

FIGS. 17A and 17B illustrate an embodiment where radio opaque braids 125 can be used to determine roll. For example, the way in which the radio opaque braids 125 are wound around the catheter 100 may be used to detect out-of-plane deflection. For example, one can detect the plane of deflection based on the frequency of the sinusoidal shape of the tantalum wire as shown in FIGS. 17A and 17B.

Figure 18A:
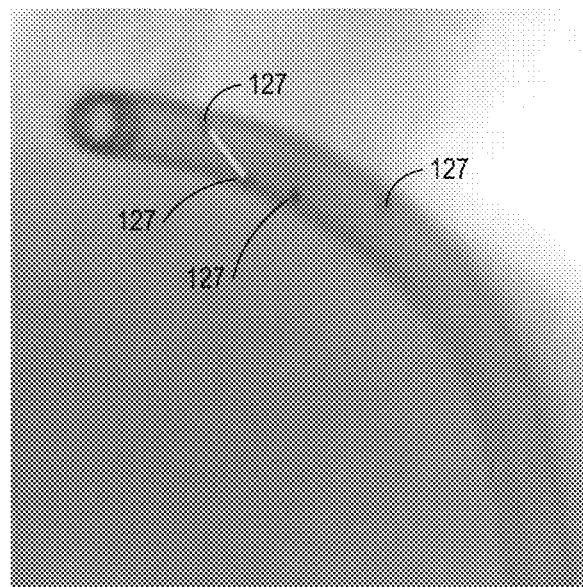
FIGS. 18A-18B illustrate another embodiment of a catheter where radio opaque markers or fiducials can be used to detect planarity.
Figure 18B:
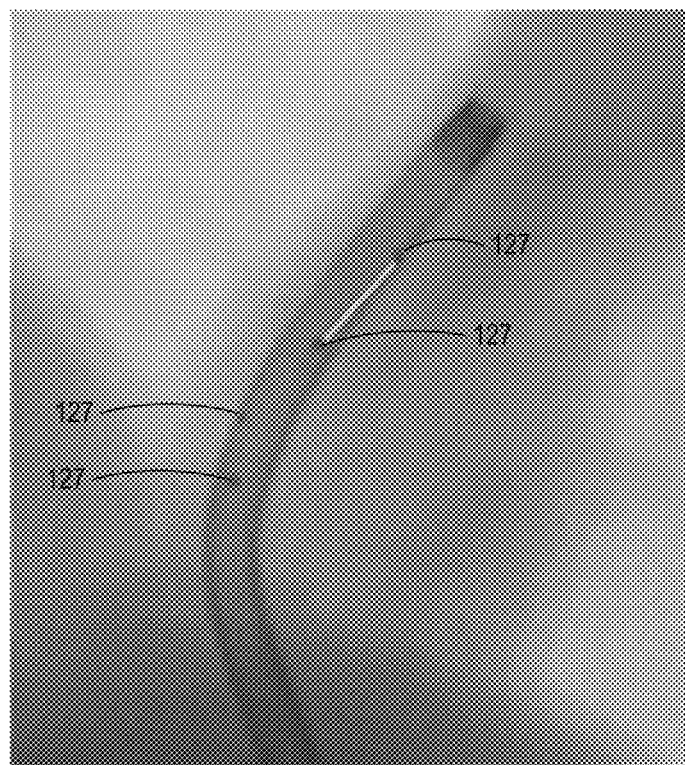

FIGS. 18A and 18B illustrate that radio opaque markers or fiducials 127 can be used to detect planarity. For example, the distance observed in a single plane can be used to provide information regarding a tool's degree of out-of-plane deflection. For example, in FIGS. 18A and 18B below, the shorter distance between the two fiducials 127 indicates bending out of plane, whereas the longer distance indicates the tool is more planar.

Figure 19:
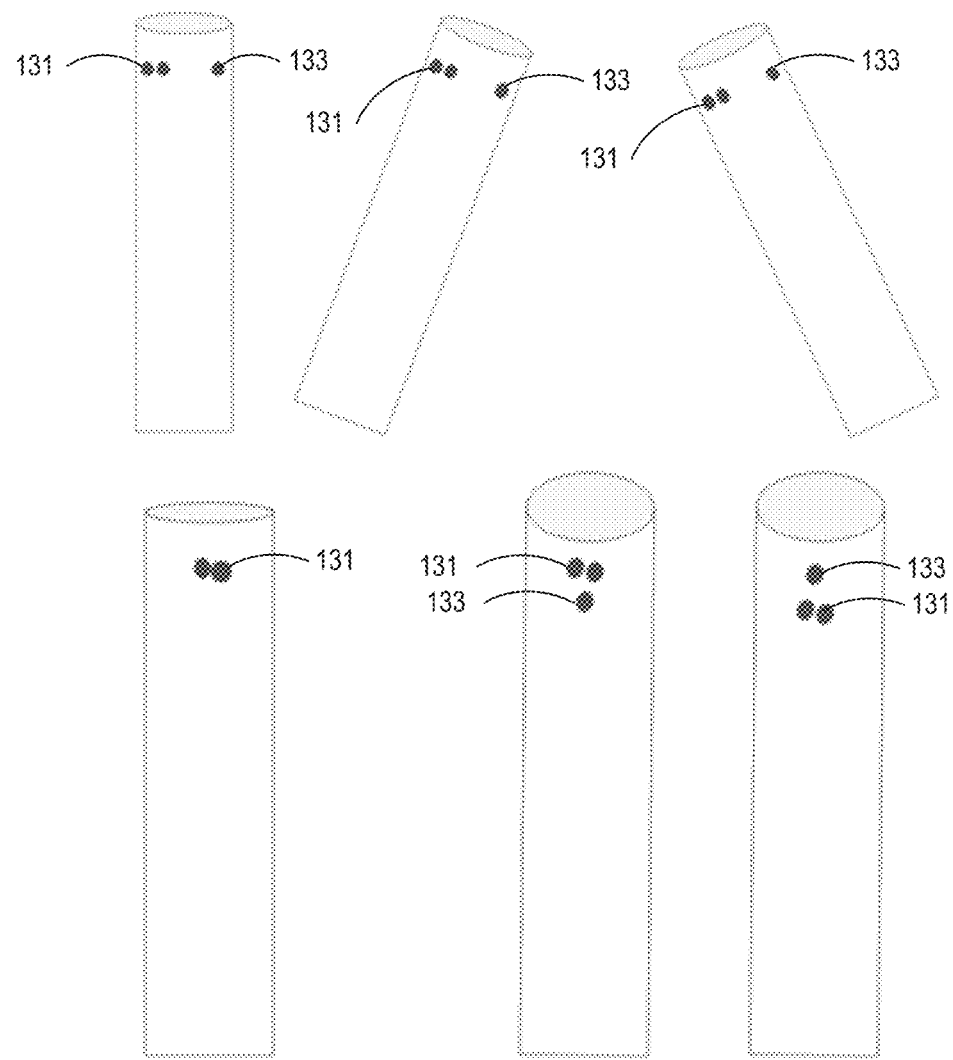
FIG. 19 illustrates another embodiment of a catheter that includes markers can be used to determine whether the catheter is angled into or out of the image plane, according to some examples.

As shown in FIG. 19 for example, by adding markers on opposite sides of the catheter that can be distinguished from one another, one can determine whether the catheter is angled into or out of the image plane. In FIG. 19, a double dot 131 is shown on one side and a single dot 133 on the other side. The first image is a side view, and the second shows the device head on (from x-ray view). When angled out of the plane, one can see the double dot 131 above the single dot 133. When angled into the plane, the single dot 133 is above the double dot 131. One may need to know the roll of the device to use this information (for example, to know which one is in front and which one is behind). With at least two pairs of front/back markers 90 degrees apart and the roll is known, one could determine this deflection for any roll value. In some embodiments, alternative markers could be used, such as shapes, for example circles, squares, donuts, lines, and or the like. Sime some embodiments, markers such as a solid ring and/or a partial ring(s) and/or the like may be used.

Safeguards Against Unexpected Catheter Motion

Unexpected motion of the distal end of a catheter can jeopardize the safety of endovascular or other procedures. The term "unexpected motion," as referred to herein, describes any movement or behavior of the distal end of a catheter that is not predicted based on the movement and/or control of the proximal end of the catheter. An example of unexpected motion may be a poor torque response where an unexpected roll motion occurs at the distal end of a catheter. The unexpected roll motion may occur when the rotation at the distal end of the catheter does not correlate to the rotation at the proximal end. For example, sometimes when the proximal end of the catheter is rotating, the distal end of the catheter may be rotating at a slower rate or may not be rotating at all. As the proximal end of the catheter continues to rotate and the distal end rotates at a slower rate or does not rotate at all, torque builds up in the catheter. If the proximal end of the catheter continues to rotate, eventually the torque in the catheter may cause the distal end of the catheter to rotate very quickly to catch up with the rotation imposed on the proximal end of the catheter and the quick rotation may be characterized as unexpected motion which could cause harm to the patient. For example, the unexpected motion at the distal end could cause damage to or a tear in a vessel wall.

As previously described, the degree of rotation of the distal end of a tool about its centerline may be informed by the addition of radio-opaque rotation fiducials. Using the methods described herein, unexpected motion at the distal end of a catheter may be prevented by tracking and comparing the rotation rate and roll of the distal and proximal ends of a catheter. In some embodiments, the comparison may be performed at discrete steps. In some embodiments, the comparison may be performed continuously. In some embodiments, rotation at the proximal end of a catheter may be prevented when there is a difference of more than a specific number of degrees of rotation between the proximal and distal ends of the catheter. By preventing further rotation after the difference in rotation is calculated at a specific amount, the system may prevent unexpected motion (for example, snapping and/or whipping of the distal end) to increase the safety of the procedure.

In some embodiments, a computer vision system may be used to identify the fiducials to model how far the distal catheter tip has rotated in relation to how far the motors controlling rotation at the proximal end of the catheter have moved. In some embodiments, this method may be paired with other safety information such as, for example, force detection and/or the like. In some embodiments, a similar method may be applied to detect discrepancies in expected advancement and retraction of the catheter as compared to actual advancement and retraction of the catheter. Use of this method may be used to identify potential obstructions to catheter motion. For example, using the methods described herein to determine the actual position a catheter tip can be compared to the expected position of a catheter tip based on how the catheter was controlled.

Automated Tool Tracking

The automated identification of a tool, tool tip and/or tool orientation may be used to control movement of a decoupled imaging source to maintain optimal viewing. For example, in an endovascular procedure, movement of an angiography system could be precisely controlled and/or centered on the tool in question without manual manipulation. In another example, in a laparoscopic surgery, movement of a camera could be precisely controlled and/or centered on the tool in question without manual manipulation. Being able to maintain optimal viewing in this manner may have the advantage of significantly better imaging for the surgeon. In some cases, automated tool tracking may improve the speed and efficiency of procedures, for example, the procedure would be faster and more efficient because the surgeon does not have to put down the tools and move the camera intermittently. In some cases, automated tool tracking may reduce the number of personal required in the operation room because no one needs to control the camera.

Automated tool tracking may be most useful for interventional and/or surgical applications where the source of input imaging is decoupled from the navigating and/or interventional tool. In these procedures, generally an assistant must manually track the surgeon's tools which may result in both lag and imprecision. For example, in an angiographic procedure, the automated tool tracking system may be used to maintain the tool tip halfway across and one third up the image screen for the entire procedure instead of the current method of having the physician put down the tools and manually readjust the screen to focus on the tool. In another example, in a laparoscopic or thoracoscopic procedure, the automated tool tracking system may be used to enable an external camera source to be automatically adjusted to maintain the tools in the center of the image, thus improving the focus and positioning of the camera.

Example Endovascular and Other Applicable Procedures

The various technologies disclosed herein related to determination of position and/or orientation determination can be used to facilitate the treatment of various diseases and other conditions where a robotic or manual device is advanced through an intraluminal (e.g., intravascular) network of a subject to reach the site of intravascular pathology (e.g., thrombosis, embolus, occlusion, aneurysm, rupture, bleeding, dissection, etc.). In some embodiments, the systems, devices, and methods described herein can be used to facilitate one or more endovascular purposes, surgeries, and/or treatments. For example, in some embodiments, the systems, processes, and methods described herein can be used for one or more of removal of intravascular blockage/reestablishment of perfusion; treatment of vessel wall injury (aneurysm and/or dissection); treatment of bleeding: aneurysm rupture/trauma; and/or the like. Moreover, in some embodiments, the systems, devices, and methods described herein can be used to treat vascular trauma.

In some embodiments, the systems, devices, and methods described herein can be used to facilitate neurovascular applications and/or treatments, such as for example to treat subarachnoid hemorrhage, aneurysm, arteriovenous malformation, and/or the like. In some embodiments, the systems, devices, and methods described herein can be used for cardiovascular applications and/or treatments, such as for example to treat myocardial infarction, coronary artery disease, pacemaker insertion, and/or the like. In some embodiments, the systems, devices, and methods described herein can be used for aortic applications and/or treatments, such as for example to treat aortic dissection, aortic aneurysm, and/or the like. In some embodiments, the systems, devices, and methods described herein can be used for peripheral emboli applications and/or treatments. In some embodiments, the systems, devices, and methods described herein can be used for vascular trauma applications and/or treatments. In some embodiments, the systems, devices, and methods described herein can be used for venous applications and/or treatments.

While the features of this application have largely been described in the context of endoluminal or endovascular procedures, the inventions described herein may also be practiced fluoroscopically guided procedures, such as endoscopic retrograde cholangiopancreatography (ERCP), discography and vertebroplasty, orthopedic and podiatric surgery, urological procedures including pyelography, intracardiac placement of intracardiac devices, ablations, and lumbar punctures.

Computer System

Figure 10:
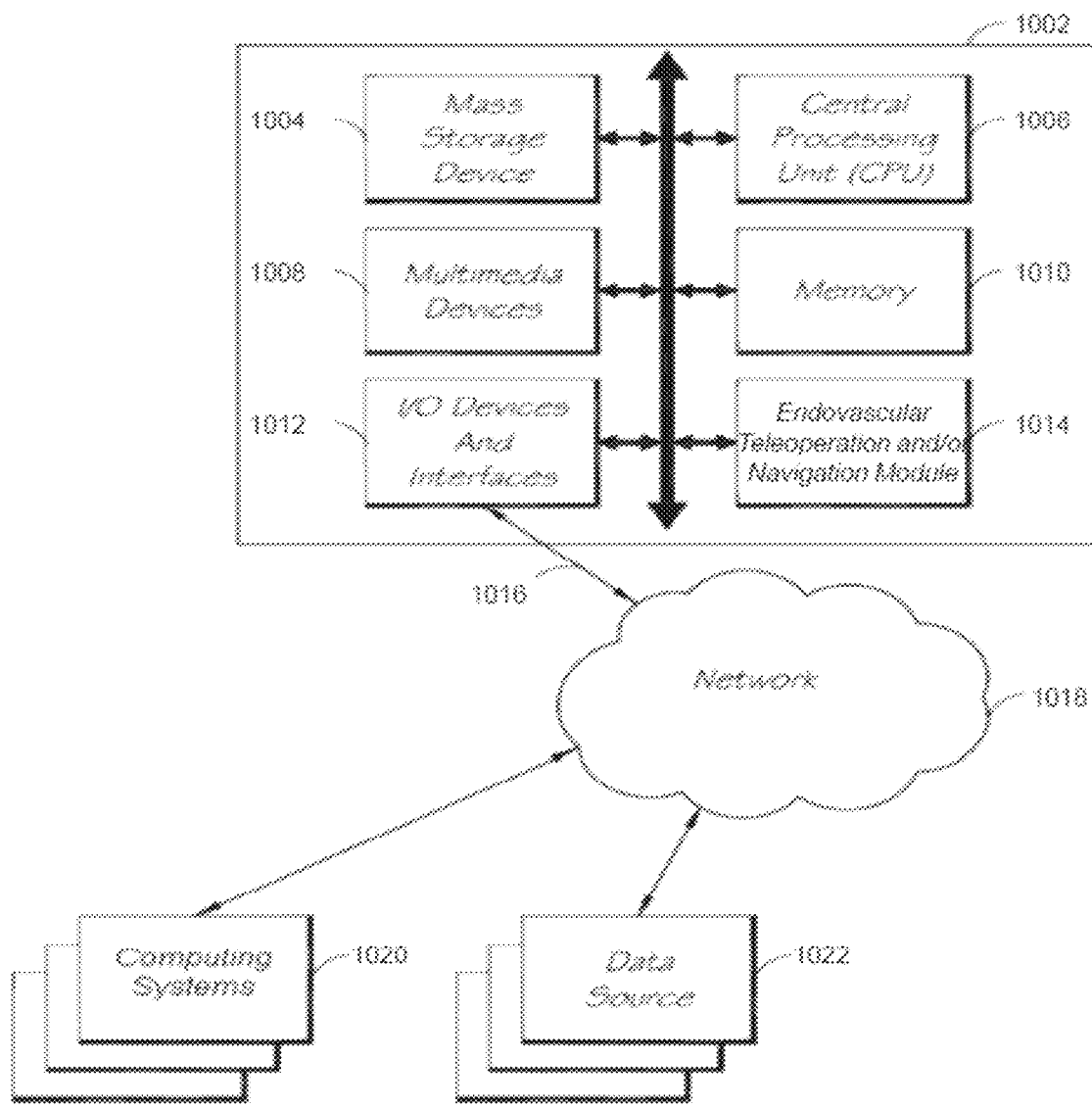
FIG. 10 is a block diagram of an embodiment of a computer system configured to implement features described herein.

In some embodiments, the systems, processes, and methods described herein are implemented using a computing system, such as the one illustrated in FIG. 10. The example computer system 1002 is in communication with one or more computing systems 1020 and/or one or more data sources 1022 via one or more networks 1018. While FIG. 10 illustrates an embodiment of a computing system 1002, it is recognized that the functionality provided for in the components and modules of computer system 1002 can be combined into fewer components and modules, or further separated into additional components and modules.

The computer system 1002 can comprise an pose determination module 1014 that carries out the functions, methods, acts, and/or processes described herein. The module 1014 is executed on the computer system 1002 by a central processing unit 1006 discussed further below.

In general the word "module," as used herein, refers to logic embodied in hardware or firmware or to a collection of software instructions, having entry and exit points. Modules are written in a program language, such as JAVA, C, C++, and/or the like. Software modules can be compiled or linked into an executable program, installed in a dynamic link library, or can be written in an interpreted language such as BASIC, PERL, LAU, PHP, or Python and/or any such languages. Software modules can be called from other modules or from themselves, and/or can be invoked in response to detected events or interruptions. Modules implemented in hardware include connected logic units such as gates and flip-flops, and/or can include programmable units, such as programmable gate arrays and/or processors.

Generally, the modules described herein refer to logical modules that can be combined with other modules or divided into sub-modules despite their physical organization or storage. The modules are executed by one or more computing systems and can be stored on or within any suitable computer readable medium, or implemented in-whole or in-part within special designed hardware or firmware. Not all calculations, analysis, and/or optimization require the use of computer systems, though any of the above-described methods, calculations, processes, or analyses can be facilitated through the use of computers. Further, in some embodiments, process blocks described herein can be altered, rearranged, combined, and/or omitted.

The computer system 1002 includes one or more processing units (CPU) 1006, which can comprise a microprocessor. The computer system 1002 further includes a physical memory 1010, such as random access memory (RAM) for temporary storage of information, a read only memory (ROM) for permanent storage of information, and a mass storage device 1004, such as a backing store, hard drive, rotating magnetic disks, solid state disks (SSD), flash memory, phase-change memory (PCM), 3D XPoint memory, diskette, or optical media storage device. Alternatively, the mass storage device can be implemented in an array of servers. Typically, the components of the computer system 1002 are connected to the computer using a standards-based bus system. The bus system can be implemented using various protocols, such as Peripheral Component Interconnect (PCI), Micro Channel, SCSI, Industrial Standard Architecture (ISA) and Extended ISA (EISA) architectures.

The computer system 1002 includes one or more input/output (I/O) devices and interfaces 1012, such as a keyboard, mouse, touch pad, and printer. The I/O devices and interfaces 1012 can include one or more display devices, such as a monitor, that allows the visual presentation of data to a user. More particularly, a display device provides for the presentation of GUIs as application software data, and multi-media presentations, for example. The I/O devices and interfaces 1012 can also provide a communications interface to various external devices. The computer system 1002 can comprise one or more multi-media devices 1008, such as speakers, video cards, graphics accelerators, and microphones, for example.

Computing System Device/Operating System

The computer system 1002 can run on a variety of computing devices, such as a server, a Windows server, a Structure Query Language server, a Unix Server, a personal computer, a laptop computer, and so forth. In other embodiments, the computer system 1002 can run on a cluster computer system, a mainframe computer system and/or other computing system suitable for controlling and/or communicating with large databases, performing high volume transaction processing, and generating reports from large databases. The computing system 1002 is generally controlled and coordinated by an operating system software, such as z/OS, Windows, Linux, UNIX, BSD, PHP, SunOS, Solaris, MacOS, ICloud services or other compatible operating systems, including proprietary operating systems. Operating systems control and schedule computer processes for execution, perform memory management, provide file system, networking, and I/O services, and provide a user interface, such as a graphical user interface (GUI), among other things.

Network

The computer system 1002 illustrated in FIG. 10 is coupled to a network 1018, such as a LAN, WAN, or the Internet via a communication link 1016 (wired, wireless, or a combination thereof). Network 1018 communicates with various computing devices and/or other electronic devices. Network 1018 is communicating with one or more computing systems 1020 and one or more data sources 1022. The pose determination module 1014 can access or can be accessed by computing systems 1020 and/or data sources 1022 through a web-enabled user access point. Connections can be a direct physical connection, a virtual connection, and other connection type. The web-enabled user access point can comprise a browser module that uses text, graphics, audio, video, and other media to present data and to allow interaction with data via the network 1018.

The output module can be implemented as a combination of an all-points addressable display such as a cathode ray tube (CRT), a liquid crystal display (LCD), a plasma display, or other types and/or combinations of displays. The output module can be implemented to communicate with input devices 1012 and they also include software with the appropriate interfaces which allow a user to access data through the use of stylized screen elements, such as menus, windows, dialogue boxes, tool bars, and controls (for example, radio buttons, check boxes, sliding scales, and so forth). Furthermore, the output module can communicate with a set of input and output devices to receive signals from the user.

Other Systems

The computing system 1002 can include one or more internal and/or external data sources (for example, data sources 1022). In some embodiments, one or more of the data repositories and the data sources described above can be implemented using a relational database, such as DB2, Sybase, Oracle, CodeBase, and Microsoft® SQL Server as well as other types of databases such as a flat-file database, an entity relationship database, and object-oriented database, and/or a record-based database.

The computer system 1002 can also access one or more databases 1022. The databases 1022 can be stored in a database or data repository. The computer system 1002 can access the one or more databases 1022 through a network 1018 or can directly access the database or data repository through I/O devices and interfaces 1012. The data repository storing the one or more databases 1022 can reside within the computer system 1002.

URLs and Cookies

In some embodiments, one or more features of the systems, methods, and devices described herein can utilize a URL and/or cookies, for example for storing and/or transmitting data or user information. A Uniform Resource Locator (URL) can include a web address and/or a reference to a web resource that is stored on a database and/or a server. The URL can specify the location of the resource on a computer and/or a computer network. The URL can include a mechanism to retrieve the network resource. The source of the network resource can receive a URL, identify the location of the web resource, and transmit the web resource back to the requestor. A URL can be converted to an IP address, and a Doman Name System (DNS) can look up the URL and its corresponding IP address. URLs can be references to web pages, file transfers, emails, database accesses, and other applications. The URLs can include a sequence of characters that identify a path, domain name, a file extension, a host name, a query, a fragment, scheme, a protocol identifier, a port number, a username, a password, a flag, an object, a resource name and/or the like. The systems disclosed herein can generate, receive, transmit, apply, parse, serialize, render, and/or perform an action on a URL.

A cookie, also referred to as an HTTP cookie, a web cookie, an internet cookie, and a browser cookie, can include data sent from a website and/or stored on a user's computer. This data can be stored by a user's web browser while the user is browsing. The cookies can include useful information for websites to remember prior browsing information, such as a shopping cart on an online store, clicking of buttons, login information, and/or records of web pages or network resources visited in the past. Cookies can also include information that the user enters, such as names, addresses, passwords, credit card information, etc. Cookies can also perform computer functions. For example, authentication cookies can be used by applications (for example, a web browser) to identify whether the user is already logged in (for example, to a web site). The cookie data can be encrypted to provide security for the consumer. Tracking cookies can be used to compile historical browsing histories of individuals. Systems disclosed herein can generate and use cookies to access data of an individual. Systems can also generate and use JSON web tokens to store authenticity information, HTTP authentication as authentication protocols, IP addresses to track session or identity information, URLs, and the like.

EMBODIMENTS

It will now be evident to those skilled in the art that there has been described herein methods, systems, and devices for improved routing of catheters and other devices to targeted anatomical locations using robotically controlled assemblies. Although the inventions hereof have been described by way of several embodiments, it will be evident that other adaptations and modifications can be employed without departing from the spirit and scope thereof. The terms and expressions employed herein have been used as terms of description and not of limitation; and thus, there is no intent of excluding equivalents, but on the contrary it is intended to cover any and all equivalents that may be employed without departing from the spirit and scope of the inventions.

While the disclosure has been described with reference to certain embodiments, it will be understood that various changes may be made, and equivalents may be substituted for elements thereof without departing from the scope of the disclosure. In addition, many modifications will be appreciated to adapt a particular instrument, situation, or material to the teachings of the disclosure without departing from the essential scope thereof. Therefore, it is intended that the disclosure is not limited to the particular embodiment disclosed as the best mode contemplated for carrying out this disclosure, but that the disclosure will include all embodiments falling within the scope of the appended claims.

Although several embodiments and examples are disclosed herein, the present application extends beyond the specifically disclosed embodiments to other alternative embodiments and/or uses of the inventions and modifications and equivalents thereof. It is also contemplated that various combinations or subcombinations of the specific features and aspects of the embodiments may be made and still fall within the scope of the inventions. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above but should be determined only by a fair reading of the claims that follow.

While the embodiments disclosed herein are susceptible to various modifications, and alternative forms, specific examples thereof have been shown in the drawings and are herein described in detail. It should be understood, however, that the inventions are not to be limited to the particular forms or methods disclosed, but, to the contrary, the inventions are to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "advancing a catheter or microcatheter" or "advancing one portion of the device (e.g., linearly) relative to another portion of the device to rotate the distal end of the device" include instructing advancing a catheter" or "instructing advancing one portion of the device," respectively. The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers. For example, "about 10 mm" includes "10 mm." Terms or phrases preceded by a term such as "substantially" include the recited term or phrase. For example, "substantially parallel" includes "parallel."

What is claimed is:

1. A computer-implemented system comprising at least one processor and at least one electronic storage medium, the electronic storage medium storing instructions configured to cause the at least one processor to:
receive, from a medical imaging device, a two-dimensional medical image, wherein the two-dimensional medical images comprises a fluoroscopic image and includes a view of at least a distal portion of a medical instrument, the distal portion of the medical instrument including one or more fiducials positioned thereon, the one or more fiducials being radio-opaque and visible in the two-dimensional medical image, wherein the one or more fiducials are configured to provide a unique two-dimensional appearance, when viewed in the two-dimensional medical image, at all roll angles of the medical instrument relative to a longitudinal axis of the medical instrument and incline angles less than 90 degrees relative to an image plane of the two-dimensional medical image;
detect, within the two-dimensional medical image, the unique two-dimensional appearance of the one or more fiducials;
based on the unique two-dimensional appearance of the one or more fiducials, determine:
a roll angle of the distal portion of the medical instrument about the longitudinal axis of medical instrument, and
an incline of the distal portion of the medical instrument relative to the plane of the two-dimensional medical image, wherein the incline includes a sign of the incline; and
based on the roll angle and the incline, generate one or more motor commands configured to cause a robotic system coupled to the medical instrument to move the medical instrument; and
cause the robotic system to move the medical instrument based on the one or more motor commands.

2. The system of claim 1, wherein the at least one processor is configured to detect the unique two-dimensional appearance of the one or more fiducials based on a computer vision algorithm.

3. The system of claim 1, wherein the at least one processor is configured to detect the unique two-dimensional appearance of the one or more fiducials using a neural network.

4. The system of claim 1, wherein the at least one processor is further configured to:
detect, within the two-dimensional medical image, a distal tip of the medical instrument; and
based on the detected distal tip of the medical instrument, determine a two-dimensional position of the distal tip of the medical instrument within the image plane of the two-dimensional medical image.

5. The system of claim 4, wherein detecting the distal tip of the medical instrument comprises:
determining, based on the two-dimensional medical image, a centerline of the distal portion of the medical instrument; and
determining an endpoint for the centerline.

6. The system of claim 1, wherein the at least one processor is further configured to:
detect, within the two-dimensional medical image, the distal portion of the medical instrument; and
based on the detected distal portion of the medical instrument, determine a heading of the medical instrument within the image plane of the two-dimensional medical image.

7. The system of claim 6, wherein determining the heading of the medical instrument comprises:
determining, based on the medical image, a centerline of the distal portion of the medical instrument; and
determining an endpoint for the centerline; and
determining a vector extending from the endpoint, the vector being colinear with a distal portion of the centerline.

8. The system of claim 1, wherein the medical instrument comprises an endoluminal medical instrument.

9. The system of claim 1, wherein the medical instrument comprises a catheter.

10. The system of claim 1, wherein the at least one processor is further configured to determine the one or more motor controls based on a user input.

11. The system of claim 1, wherein the at least one processor is further configured to cause the determined roll angle or the determined incline to be displayed on a user display.

12. The system of claim 11, wherein the at least one processor is further configured to cause the two-dimensional medical image to be displayed on the user display.

13. A method comprising:
receiving, from a medical imaging device, a two-dimensional medical image wherein the two-dimensional medical image comprises a fluoroscopic image and includes a view of at least a distal portion of a medical instrument, the distal portion of the medical instrument including one or more fiducials positioned thereon, the one or more fiducials being radio-opaque and visible in the medical image, wherein the one or more fiducials are configured to provide a unique two-dimensional appearance, when viewed under fluoroscopy, at all roll angles of the medical instrument relative to a longitudinal axis of the medical instrument and incline angles less than 90 degrees relative to an image plane of the two-dimensional medical image;
detecting, within the two-dimensional medical image, unique two-dimensional appearance of the one or more fiducials;
based on the unique two-dimensional appearance of the one or more fiducials, determining:
a roll angle of the distal portion of the medical instrument about the longitudinal axis of medical instrument, and
an incline of the distal portion of the medical instrument relative to the plane of the two-dimensional medical image, wherein the incline includes a sign of the incline;
based on the roll angle and the incline, generating one or more motor commands configured to cause a robotic system coupled to the medical instrument to move the medical instrument; and
causing the robotic system to move the medical instrument based on the one or more motor commands.

14. The method of claim 13, wherein detecting the unique two-dimensional appearance of the one or more fiducials is based on a computer vision algorithm.

15. The method of claim 13, detecting the unique two-dimensional appearance of the one or more fiducials is based on a neural network.

16. The method of claim 13, further comprising:
    detecting, within the two-dimensional medical image, a distal tip of the medical instrument; and
    based on the detected distal tip of the medical instrument, determining a two-dimensional position of the distal tip of the medical instrument within the image plane of two-dimensional medical image.

17. The method of claim 16, wherein detecting the distal tip of the medical instrument comprises:
    determining, based on the two-dimensional medical image, a centerline of the distal portion of the medical instrument; and
    determining an endpoint for the centerline.

18. The method of claim 13, further comprising:
    detecting, within the two-dimensional medical image, the distal portion of the medical instrument; and
    based on the detected distal portion of the medical instrument, determining a heading of the medical instrument within the image plane of the two-dimensional medical image.

19. The method of claim 18, wherein determining the heading of the medical instrument comprises:
    determining, based on the two-dimensional medical image, a centerline of the distal portion of the medical instrument; and
    determining an endpoint for the centerline; and
    determining a vector extending from the endpoint, the vector being colinear with a distal portion of the centerline.

20. The method of claim 13, wherein the medical instrument comprises a catheter.

* * * * *